(12) United States Patent
Dunnam et al.

(10) Patent No.: US 8,968,539 B2
(45) Date of Patent: Mar. 3, 2015

(54) METHODS FOR VOLTAGE-INDUCED PROTEIN INCORPORATION INTO PLANAR LIPID BILAYERS

(75) Inventors: Ryan Dunnam, San Diego, CA (US); Geoffrey Barrall, San Diego, CA (US); Melissa Poquette, Temecula, CA (US)

(73) Assignee: Electronic Biosciences, Inc., San Diego, CA (US)

(*) Notice: Subject to any disclaimer, the term of this patent is extended or adjusted under 35 U.S.C. 154(b) by 421 days.

(21) Appl. No.: 13/414,636

(22) Filed: Mar. 7, 2012

(65) Prior Publication Data

US 2012/0255862 A1  Oct. 11, 2012

Related U.S. Application Data

(60) Provisional application No. 61/450,475, filed on Mar. 8, 2011.

(51) Int. Cl.
| | | |
|---|---|---|
| G01N 27/49 | (2006.01) | |
| B82Y 40/00 | (2011.01) | |
| B82Y 5/00 | (2011.01) | |
| B82Y 15/00 | (2011.01) | |
| G01N 33/68 | (2006.01) | |
| G01N 33/92 | (2006.01) | |

(52) U.S. Cl.
CPC . B82Y 40/00 (2013.01); B82Y 5/00 (2013.01); B82Y 15/00 (2013.01); G01N 27/49 (2013.01); G01N 33/68 (2013.01); G01N 33/92 (2013.01)
USPC .......................................... 204/451; 204/601

(58) Field of Classification Search
None
See application file for complete search history.

(56) References Cited

U.S. PATENT DOCUMENTS

| | | |
|---|---|---|
| 7,569,850 B2 | 8/2009 | Noy et al. |
| 7,745,856 B2 | 6/2010 | Noy et al. |
| 7,777,505 B2 | 8/2010 | White et al. |
| 2004/0023372 A1 | 2/2004 | Klein et al. |
| 2004/0052857 A1 | 3/2004 | Keating et al. |
| 2006/0169975 A1 | 8/2006 | Noy et al. |
| 2008/0153150 A1 | 6/2008 | Holden et al. |
| 2008/0218184 A1* | 9/2008 | White et al. .................. 324/693 |
| 2009/0274870 A1 | 11/2009 | Harnack et al. |
| 2010/0065822 A1 | 3/2010 | Noy et al. |
| 2010/0233781 A1 | 9/2010 | Bangera et al. |
| 2011/0162963 A1 | 7/2011 | Hibbs et al. |
| 2011/0177154 A1 | 7/2011 | Bangera et al. |
| 2011/0193249 A1 | 8/2011 | Chen et al. |
| 2011/0268791 A1 | 11/2011 | Liu et al. |
| 2012/0114925 A1 | 5/2012 | Harnack et al. |

OTHER PUBLICATIONS

Benz et al., "Reversible Electrical Breakdown of Lipid Bilayer Membranes: A Charge-Pulse Relaxation Study," J. Membrane Biol. 48, 181-204 (1979).

Heron et al, "Simultaneous measurement of ionic current and fluorescence from single protein pores," J. Am. Chem. Soc. 131:1652-1653 (2009).

(Continued)

*Primary Examiner* — J. Christopher Ball
(74) *Attorney, Agent, or Firm* — Grant IP, Inc.

(57) ABSTRACT

Disclosed here are methods useful for incorporating protein into lipid bilayers using voltage induced insertion. The methods presented herein can decrease time and costs associated with incorporation of proteins into naturally derived or artificially created lipid bilayers. A method for incorporating a protein capable of translocating a ligand also is disclosed herein.

18 Claims, 8 Drawing Sheets

(56) References Cited

OTHER PUBLICATIONS

Renner et al., "Voltage-controlled insertion of single-hemolysin and *Mycobacterium smegmatis* nanopores into lipid bilayer membranes," Applied Physics Letters 98, 083701 2011.

Tung et al., "Changes in Electroporation Thresholds of Lipid Membranes by Surfactants and Peptides", Ann N Y Acad Sci. Oct. 30, 1999;888:249-65.

White et al., "Single ion-channel recordings using glass nanopore membranes," J. Am. Chem. Soc. 2007, 129, (38), 11766-11775).

* cited by examiner

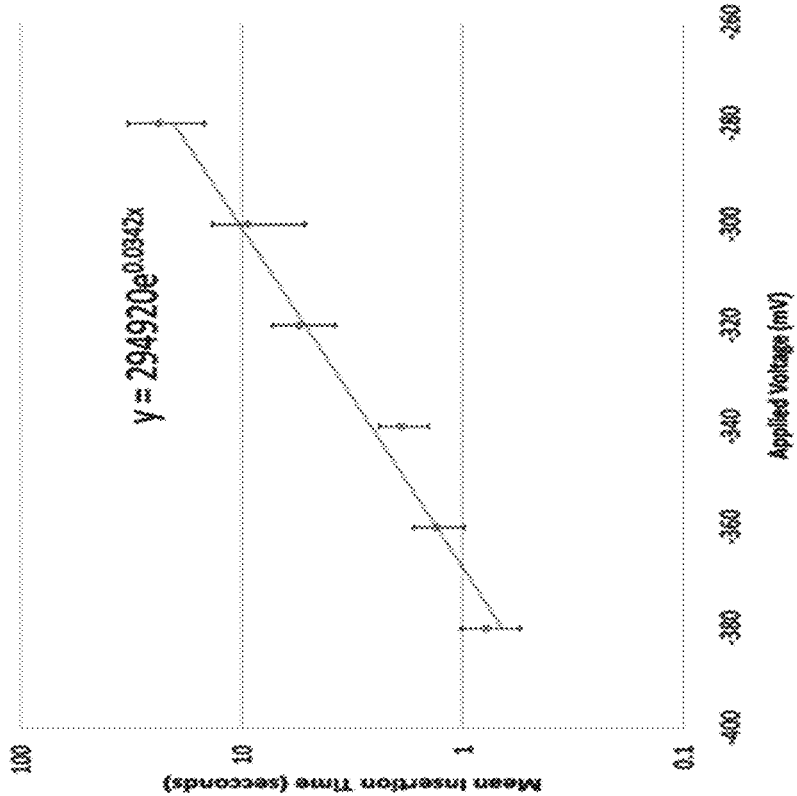
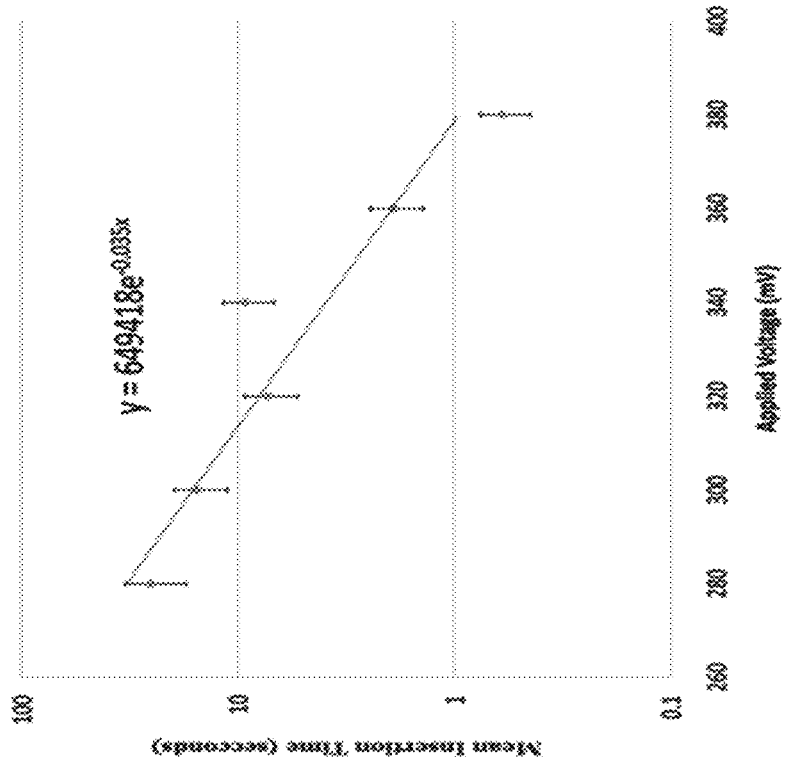
Figure 6A
Figure 6B

```
                              SEQUENCE LISTING

<160> NUMBER OF SEQ ID NOS: 5

<210> SEQ ID NO 1
<211> LENGTH: 293
<212> TYPE: PRT
<213> ORGANISM: Staphylococcus aureus

<400> SEQUENCE: 1

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 2
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 2

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Lys Asn His
        35                  40                  45

Asn Lys Lys Leu Leu Val Ile Arg Thr Lys Thr Ile Ala Gly Gln
    50                  55                  60

Tyr Arg Val Tyr Ser Glu Glu Gly Ala Asn Lys Ser Gly Leu Ala Trp
65              70                  75                  80

Pro Ser Ala Phe Lys Val Gln Leu Gln Leu Pro Asp Asn Glu Val Ala
            85                  90                  95

Gln Ile Ser Asp Tyr Tyr Pro Arg Asn Ser Ile Asp Thr Lys Glu Tyr
            100                 105                 110

Lys Ser Thr Leu Thr Tyr Gly Phe Asn Gly Asn Val Thr Gly Asp Asp
            115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
            165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
            245                 250                 255

Gln Leu His Trp Thr Ser Thr Asn Trp Lys Gly Thr Asn Thr Lys Asp
        260                 265                 270

Lys Trp Thr Asp Arg Ser Ser Glu Arg Tyr Lys Ile Asp Trp Glu Lys
            275                 280                 285

Glu Glu Met Thr Asn
        290

<210> SEQ ID NO 3
<211> LENGTH: 885
<212> TYPE: DNA
<213> ORGANISM: Staphylococcus aureus

<400> SEQUENCE: 3
atggcagatt ctgatattaa tattaaaacc ggtactacag atattggaag caatactaca    60
gtaaaaacag gtgatttagt cacttatgat aaagaaaatg gcatgcacaa aaaagtattt   120 tatagttta tcgatgataa aaatcacaat aaaaaactgc tagttattag aacgaaaggt   180
accattgctg gtcaatatag agtttatagc gaagaaggtg ctaacaaaag tggtttagcc   240
tggccttcag cctttaaggt acagttgcaa ctacctgata tgaagtagc tcaaatatct   300 gattactatc caagaaattc gattgataca aaagagtata tgagtacttt aacttatgga   360
```

```
ttcaacggta atgttactgg tgatgataca ggaaaaattg gcggcctta t tggtgcaaat      420 gtttcgattg gtcatacact gaaatatgtt caacctgatt tcaaaacaat tttagagagc      480
ccaactgata aaaagtagg ctggaaagtg atatttaaca atatggtcaa tcaaaattgg       540
ggaccatatg atagagattc ttggaacccg gtatatggca atcaactttt catgaaaact      600
agaaatggtt ctatgaaagc agcagataac ttccttgatc ctaacaaagc aagttctcta      660
ttatcttcag ggttttcacc agacttcgct acagttatta ctatggatag aaaagcatcc      720
aaacaacaaa caaatataga tgtaaatatac gaacgagttc gtgatgatta ccaattgcat     780
tggacttcaa caaattggaa aggtaccaat actaaagata aatggacaga tcgttcttca      840
gaaagatata aaatcgattg ggaaaaagaa gaaatgacaa attaa                      885
```

<210> SEQ ID NO 4
<211> LENGTH: 885
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
atggcagatt ctgatattaa tattaaaacc ggtactacag atattggaag caatactaca      60
gtaaaaacag gtgatttagt cacttatgat aaagaaaatg gcatgcacaa aaaagtatt t   120 tatagttta tcgatgataa aaatcacaat aaaaaactgc tagttattag aacgaaaggt      180
accattgctg gtcaatatag agtttatagc gaagaaggtg ctaacaaaag tggtttagcc      240
tggccttcag ccttta aggt acagttgcaa ctacctgata tgaagtagc tcaaatatct     300 gattactatc caagaaattc gattgataca aagagtata agagtacttt aacttatgga     360
ttcaacggta atgttactgg tgatgataca ggaaaaattg gcggcctta t tggtgcaaat   420 gtttcgattg gtcatacact gaaatatgtt caacctgatt tcaaaacaat tttagagagc    480
ccaactgata aaaagtagg ctggaaagtg atatttaaca atatggtcaa tcaaaattgg     540
ggaccatatg atagagattc ttggaacccg gtatatggca atcaactttt catgaaaact    600
agaaatggtt ctatgaaagc agcagataac ttccttgatc ctaacaaagc aagttctcta   660
ttatcttcag ggttttcacc agacttcgct acagttatta ctatggatag aaaagcatcc   720
aaacaacaaa caaatataga tgtaaatatac gaacgagttc gtgatgatta ccaattgcat   780
tggacttcaa caaattggaa aggtaccaat actaaagata aatggacaga tcgttcttca   840
gaaagatata aaatcgattg ggaaaaagaa gaaatgacaa attaa                     885
```

<210> SEQ ID NO 5
<211> LENGTH: 100
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

```
tttttttttt tttttttttt tttttttttt tttttttttt tttttttttt tttttttttt     60
tttttttttt tttttttttt tttttttttt tttttttttt                          100
```

METHODS FOR VOLTAGE-INDUCED PROTEIN INCORPORATION INTO PLANAR LIPID BILAYERS

RELATED PATENT APPLICATION

This patent application claims the benefit of U.S. Provisional Patent Application No. 61/450,475 filed on Mar. 8, 2011, entitled "METHODS FOR VOLTAGE-INDUCED PROTEIN INCORPORATION INTO PLANAR LIPID BILAYERS," naming Geoffrey Barrall, Ryan Dunnam and Melissa Poquette as inventors. The entire content of the foregoing patent application is incorporated herein by reference, including all text, tables and drawings.

SEQUENCE LISTING

The instant application contains a Sequence Listing which has been submitted in ASCII format via EFS-Web and is hereby incorporated by reference in its entirety. Said ASCII copy, created on Jun. 15, 2012, is named EBS-1002-UT.txt and is 8,454 bytes in size.

FIELD

The technology relates in part to formation of pores in lipid bilayers, and in some embodiments, to voltage-induced insertion of proteins into planar lipid bilayers that form pores or channels.

BACKGROUND

Measurement of single ion channel conductance in planar lipid bilayers (PLBs), formed across a nanometer or micrometer (μm) scale aperture, is part of research pertaining to DNA sequencing, chemical sensing, biophysics, medicine and drug discovery. Isolation of a single ion channel in a bilayer allows for detailed measurements of channel conductivity and studies of analytes interacting with the channel. Single ion channels in bilayers also provide for the study of ion channel structure and function through measurement of channel conductance and gating.

SUMMARY

Provided in some embodiments are methods that comprise contacting a planar lipid bilayer (PLB) with a protein capable of inserting into the lipid bilayer, applying an electrical bias at an insertion voltage of about 160 millivolts (mV) or greater, monitoring for the presence of an insertion of a protein into the PLB, and reducing the voltage of the electrical bias to less than the insertion voltage (e.g., at least 1 mV lower than the insertion voltage) once a protein insertion is observed. Also provided in certain embodiments are methods that comprise contacting a PLB disposed between electrodes with a protein capable of inserting into the lipid bilayer, applying an insertion voltage bias between the electrodes of about 160 mV or greater, monitoring for the presence of an insertion of a protein into the PLB, and reducing the voltage to less than the insertion voltage after protein insertion is observed. In some embodiments the voltage is reduced by at least 1 mV lower than the insertion voltage after an insertion is observed.

In some embodiments, the applied insertion voltage or insertion voltage bias is about 160 mV or greater. In certain embodiments, the applied voltage bias is about 165 mV or greater, about 170 mV or greater, about 175 mV or greater, about 180 mV or greater, about 185 mV or greater, about 190 mV or greater, about 195 mV or greater, about 200 mV or greater, about 220 mV or greater, about 240 mV or greater, about 260 mV or greater, about 280 mV or greater, about 300 mV or greater, about 320 mV or greater, about 340 mV or greater, about 350 mV or greater, about 360 mV or greater, about 380 mV or greater, about 400 mV or greater, about 420 mV or greater, about 440 mV or greater, about 460 mV or greater, about 480 mV or greater, about 500 mV or greater, about 520 mV or greater, about 540 mV or greater, about 560 mV or greater, about 580 mV or greater, about 600 mV or greater, about 620 mV or greater, about 640 mV or greater, about 660 mV or greater, about 680 mV or greater, about 700 mV or greater, about 720 mV or greater, about 740 mV or greater, about 760 mV or greater, about 780 mV or greater, about 800 mV or greater, about 900 mV or greater, about 1000 mV or greater, or about 2000 mV or greater. In some embodiments, the applied voltage or voltage bias is about 160 mV to about 2000 mV. In some embodiments, the voltage or voltage bias is about 200 mV to about 500 mV. In certain embodiments, the voltage or voltage bias is about 350 mV. In some embodiments, the insertion voltage is greater than 300 mV (e.g., about 305 mV, 310 mV, 320 mV or greater).

In embodiments where the voltage is reduced after applying an insertion voltage, the voltage is reduced by about 1 mV to about 500 mV (e.g., reducing the insertion by about 5 mV, 10 mV, 15 mV, 20 mV, 25 mV, 30 mV, 40 mV, 50 mV, 60 mV, 70 mV, 80 mV, 90 mV, 100 mV, 200 mV, 300 mV, 400 mV). For example, (i) in embodiments where the insertion voltage is about +160 mV, the voltage may be reduced to about +120 mV, and (ii) in embodiments where the insertion voltage is about −160 mV, the voltage may be reduced to about −120 mV.

In certain embodiments, methods include toggling the voltage. In some embodiments, the voltage is toggled multiple times. In certain embodiments, the voltage is toggled 2 or more times, 3 or more times, 4 or more times, 5 or more times, 10 or more times, 25 or more times, 50 or more times, 100 or more times, 500 or more times, 1,000 or more times, 5,000 or more times, 10,000 or more times, 25,000 or more times, 50,000 or more times, 100,000 or more times, 250,000 or more times, 500,000 or more times, 750,000 or more times, or up to about 1,000,000 times or greater. The voltage often is toggled before protein insertion in a PLB, and sometimes during and/or after protein insertion in a PLB.

In some embodiments, each toggle cycle, or each insertion voltage duration, reduced voltage duration, measurement voltage duration or resting voltage duration, is about 1 milliseconds to about 5 seconds or greater (e.g., about 1 millisecond, about 5 milliseconds, about 10 milliseconds, about 15 milliseconds, about 20 milliseconds, about 25 milliseconds, about 50 milliseconds, about 100 milliseconds, about 200 milliseconds, about 250 milliseconds, about 300 milliseconds, about 350 milliseconds, about 400 milliseconds, about 450 milliseconds, about 500 milliseconds, about 600 milliseconds, about 700 milliseconds, about 800 milliseconds, about 900 milliseconds, about 1 second, about 2 seconds about 3 seconds, about 4 seconds or about 5 seconds or greater). In certain embodiments, the voltage is toggled in a timeframe of about 1 milliseconds to about 180 minutes or greater (e.g., about 1 millisecond, about 5 milliseconds, about 10 milliseconds, about 25 milliseconds, about 50 milliseconds, about 100 milliseconds, about 200 milliseconds, about 250 milliseconds, about 300 milliseconds, about 350 milliseconds, about 400 milliseconds, about 450 milliseconds, about 500 milliseconds, about 600 milliseconds, about 700 milliseconds, about 800 milliseconds, about 900 milliseconds, about 1 second, about 2 seconds about 3 seconds, about 4 seconds, about 5 seconds, about 10 seconds, about 20 seconds, about 30 seconds, about 40 seconds, about 50 seconds, about 1 minute, about 2 minutes, about 3 minutes, about 4 minutes, about 5 minutes, about 10 minutes, about 20 minutes, about 30 minutes, about 40 minutes, about 50 minutes, about 60 minutes, about 70 minutes, about 80 minutes, about 90 minutes, about 100 minutes, about 110 minutes, about 120 minutes, about 130 minutes, about 140 minutes, about 150 minutes, about 160 minutes, about 170 minutes, or up to about 180 minutes or greater). In some embodiments, the voltage is toggled until protein insertion into the bilayer is identified. In some embodiments, an insertion voltage duration is greater than 20 milliseconds and in some embodiments, an insertion voltage duration is less than 20 milliseconds.

In certain embodiments, a positive voltage bias is included in the toggling. In some embodiments, a negative voltage bias is included in the toggling. In certain embodiments, a positive voltage bias and a negative voltage bias is included in the toggling. In some embodiments, the positive voltage bias and the negative voltage bias are alternated. In certain embodiments, each cycle in the toggling includes applying an insertion voltage bias followed by applying a measurement voltage bias (e.g., a voltage at which protein insertion in a PLB can be measured or observed). In some embodiments involving toggling, the voltage is reduced to about 0 mV (a "resting voltage," e.g., about −5 mV to about +5 mV) after an insertion voltage is applied. In certain embodiments that involve toggling, a resting voltage is not applied until a protein insertion event is identified. In some embodiments, the voltage is reduced to a resting voltage after an insertion voltage is applied and after a protein insertion event is identified.

In some embodiments, methods include monitoring for insertion of the protein into the lipid bilayer. In certain embodiments, the insertion is identified by a stable current at an open pore current level. In some embodiments, the insertion is identified by one or more transient voltage spikes. In certain embodiments, the protein remains stably inserted into the PLB for a useful period of time from the time the first voltage is applied. In some embodiments, the period of time is about 5 seconds or greater, and in certain embodiments, the period of time is about 1 hour or greater (e.g., about 5 seconds or greater, about 10 seconds or greater, about 20 seconds or greater, about 30 seconds or greater, about 40 seconds or greater, about 50 seconds or greater, about 1 minute (60 seconds) or greater, about 2 minutes or greater, about 3 minutes or greater, about 4 minutes or greater, about 5 minutes or greater, about 10 minutes or greater, about 15 minutes or greater, about 20 minutes or greater, about 25 minutes or greater, about 30 minutes or greater, about 35 minutes or greater, about 40 minutes or greater, about 45 minutes or greater, about 50 minutes or greater, about 55 minutes or greater, about 60 minutes or greater (e.g., about 1 hour or greater), about 2 hours or greater, about 3 hours or greater about 4 hours or greater or about 5 hours or greater).

In various embodiments, the protein is stably inserted into the PLB within a relatively short period of time from the time the first insertion bias is applied. In some embodiments, the period of time is 1 hour or less (e.g., 1 hour or less (60 minutes), 50 minutes or less, 40 minutes or less, 30 minutes or less, 20 minutes or less, 15 minutes or less, 10 minutes or less, 5 minutes or less, 4 minutes or less, 3 minutes or less, 2 minutes or less, 1 minute or less, 50 seconds or less, 40 seconds or less, 30 seconds or less, 20 seconds or less, 15 seconds or less, 10 seconds or less, or 5 seconds or less).

In some embodiments, a single protein inserts into a PLB. In certain embodiments, two or more proteins insert into a PLB (e.g., about 2, 3, 4, 5, 6, 7, 8, 9 or 10 protein molecules insert into the bilayer), and sometimes the two or more protein molecules are the same type of protein or different types of protein (e.g., 2, 3, 4, 5, 6, 7, 8, 9 or 10 different types of proteins).

In some embodiments, the protein contacted with and inserted in a PLB comprises a pore or channel. In certain embodiments, the protein is an ion channel protein. In certain embodiments, the protein is a porin. In some embodiments, a nucleic acid is translocated through a porin protein. In certain embodiments, the porin protein is a hemolysin protein. In some embodiments, the porin protein is a bacterial hemolysin protein. In certain embodiments, the porin protein is an alpha hemolysin protein. In some embodiments, the protein is a native protein. In certain embodiments, the protein includes one or more amino acid insertions, deletions or substitutions with respect to a native counterpart.

In some embodiments, the protein is incorporated into a vesicle prior to contacting the protein with the PLB. In certain embodiments, the PLB contacted with the protein prior to applying an electrical bias includes substantially no inserted protein. In various embodiments, insertion is conducted at a substantially constant back pressure. One or more of insertion, monitoring for insertion, and measuring analyte interaction in a nanopore membrane system are conducted at about atmospheric pressure, in some embodiments. In certain embodiments, the protein concentration in a solution contacting a PLB is about 0.001 femtomolar (fM) to about 10 millimolar (e.g., about 0.001 fM, 0.005 fM, about 0.010 fM, about 0.015 fM, about 0.020 fM, about 0.025 fM, about 0.050 fM, about 0.075 fM, about 0.1 fM, about 0.2 fM, about 0.3 fM, about 0.4 fM, about 0.5 fM, about 0.6 fM, about 0.7 fM, about 0.8 fM, about 0.9 fM, about 1 fM, about 1.5 fM, about 2 fM, about 2.5 fM, about 3 fM, about 3.5 fM, about 4 fM, about 4.5 fM, about 5 fM, about 10 fM, about 20 fM, about 30 fM, about 40 fM, about 50 fM, about 100 fM, about 150 fM, about 200 fM, about 250 fM, about 300 fM, about 350 fM, about 400 fM, about 450 fM, about 500 fM, about 550 fM, about 600 fM, about 650 fM, about 700 fM, about 750 fM, about 800 fM, about 850 fM, about 900 fM, about 950 fM, about 1000 fM (e.g., about 1 picomolar (pM)), about 10 pM, about 50 pM, about 100 pM, about 250 pM, about 500 pM, about 750 pM, or about 1000 pM (e.g., about 1 nanomolar (nM)), about 5 nM, about 10 nM, about 20 nM, about 30 nM, about 40 nM, about 50 nM, about 60 nM, about 70 nM, about 80 nM, about 90 nM, about 100 nM, about 150 nM, about 200 nM, about 250 nM, about 300 nM, about 350 nM, about 400 nM, about 450 nM, about 500 nM, about 600 nM, about 700 nM, about 800 nM, about 900 nM, or about 1000 nM (e.g., 1 micromolar (µM)), about 5 µM, about 10 µM, about 50 µM, about 100 µM, about 250 µM, about 500 µM, about 750 µM, or about 1000 µM (e.g., about 1 millimolar (mM)), about 2 mM, about 3 mM, about 4 mM, about 5 mM, about 6 mM, about 7 mM, about 8 mM, about 9 mM or about 10 mM).

In some embodiments, a lipid bilayer has substantially no protein associated with it, often prior to voltage-induced protein insertion. In certain embodiments, the lipid bilayer has one or more proteins already inserted into the lipid bilayer prior to voltage-induced protein insertion.

In certain embodiments, the protein is in contact with a ligand. The ligand sometimes is capable of translocating the protein (e.g., through the protein and across the lipid bilayer). In some embodiments, the ligand comprises a nucleic acid. In certain embodiments, insertion into a lipid bilayer is identified by a protein blocking event. In some embodiments, the protein blocking event is a water soluble chemical compound blocking event. In some embodiments, the water soluble chemical compound is an organic molecule, a protein, a chemical weapons agent, a toxic chemical, a pharmaceutical, a metal ion, a cation, an anion, a nanoparticle, an amino acid or a mononucleoside.

In certain embodiments, the PLB spans an aperture of a channel in a membrane separating two fluid reservoirs. In some embodiments, the aperture of the channel is a micron scale aperture in a membrane. In some embodiments, the aperture of the channel is a nanoscale aperture or nanopore in a membrane. In some embodiments, the membrane comprises glass, Si, $SiO_2$, $Si_3N_4$, alumina, nitrides, diamond, quartz, sapphire metals, ceramics, alumino-silicate, polymers (e.g., Teflon, polycarbonate) or combinations thereof. In some embodiments, the aperture is in a channel or nanopore in a glass or quartz membrane. In certain embodiments, the channel or nanopore has a diameter of about 0.25 nanometer to about 50 μm (e.g., about 0.25 nanometers, about 0.5 nanometers, about 1 nanometer, about 1.5 nanometers, about 2 nanometers, about 2.5 nanometers, about 3 nanometers, about 3.5 nanometers, about 4 nanometers, about 4.5 nanometers, about 5 nanometers, about 6 nanometers, about 7 nanometers, about 8 nanometers, about 9 nanometers, about 10 nanometers, about 15 nanometers, about 20 nanometers, about 25 nanometers, about 30 nanometers, about 35 nanometers, about 40 nanometers, about 45 nanometers, about 50 nanometers, about 60 nanometers, about 70 nanometers, about 80 nanometers, about 90 nanometers, about 100 nanometers, about 125 nanometers, about 150 nanometers, about 175 nanometers, about 200 nanometers, about 250 nanometers, about 300 nanometers, about 350 nanometers, about 350 nanometers, about 400 nanometers, about 500 nanometers, about 600 nanometers, about 700 nanometers, about 800 nanometers, about 900 nanometers, about 1000 nanometers (e.g., 1 μm), about 1.5 μms, about 2 μms, about 2.5 μms, about 3 μm, about 3.5 μms, about 4 μm, about 5 μm, about 10 μm, about 15 μm, about 20 μm, about 25 μm, about 30 μm, about 35 μm, about 40 μm, about 45 μm, or about 50 μm). In certain embodiments, the channel or nanopore has a diameter of about 1 nanometer to about 4 μm.

Certain embodiments are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIGS. 6A and 6B graphically illustrate the voltage dependence of mean time to insertion of alpha-HL into a PLB using a 35 nM monomeric alpha-HL solution. Experimental details and results are described in Example 3.

DETAILED DESCRIPTION

Figure 1:
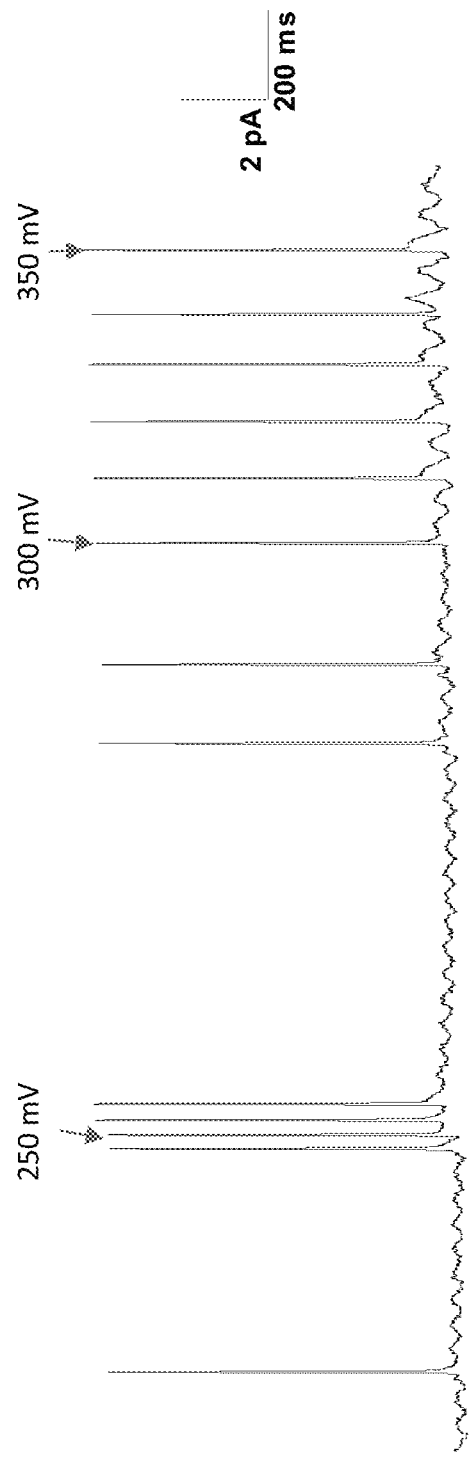
FIG. 1 graphically illustrates the results of stepping the voltage on a phospholipid bilayer (PLB) on a glass nanopore membrane (GNM) in discrete 10 mV increments from 230 mV to 350 mV. Experimental details and results are described in Example 2.

Bilayer platforms currently used by many researchers typically have apertures of between about 100 μm and 200 μm in diameter in a thin film. The large aperture and large capacitance of the bilayer often leads to elevated noise levels that mask the ion channel current and also can limit the range of protein pores and protein pore properties that can be studied. Large area bilayers sometimes are fragile and typically are isolated from shock, vibration and significant voltage or pressure differentials in order to make single channel recordings of ion channel conductance. Significantly reducing the size of the aperture across which the PLB is formed improves the noise performance and robustness of the PLB.

Utilization of bilayers with small apertures (e.g., less than about 100 μm in diameter) sometimes also has certain disadvantages. The reduced bilayer area requires the use of significantly more protein to achieve a single insertion. An increased amount of channel protein is particularly problematic when recombinant proteins are used, since it can be difficult to produce significant quantities of protein with many expression methods. For PLBs with a diameter under about 2 μm, it has proven difficult to obtain protein insertions from bacterial porins such as alpha-hemolysin (alpha-HL) from *staphylococcus aureus* expressed using small scale bench-top methods such as in vitro transcription and translation (IVTT).

Concentrations ranging from about 0.5 μM to about 2 μM have been reported for insertion into PLBs of about 150 μm in diameter. For 20 to 25 μm diameter apertures, protein concentrations of about 20 nM are needed for protein insertion, while pores with a sub-micron diameter often need between about 0.5 μM to 3 μM concentration of alpha-HL to obtain insertions within minutes. The reduction in aperture diameter from 150 μm to about 0.5 μm leads to an almost 1,000,000 fold increase in the concentration of the protein necessary for rapid insertion times (e.g., within minutes). For proteins that are produced in small quantities, such a large increase in the amount of protein needed for rapid insertion sometimes is problematic if not completely prohibitive. Another consideration in the utilization of PLBs for analysis using single channel recordings is the maintenance of a single channel in the bilayer. High concentrations of proteins sometimes lead to additional insertions in the bilayer, before data can be taken with the first channel. White et al (J. Am. Chem. Soc. 2007, 129, (38), 11766-11775) have described a glass nanopore membrane (GNM) system that uses a back pressure on the order of 10 to 200 mmHg to promote protein insertion into the PLB on the aperture of the GNM. Upon insertion, the pressure is reduced to prevent subsequent insertion. White et al. also have shown that reducing the back pressure below a critical level causes proteins in the PLB to come out. In practice, additional channel insertions often occur within minutes after the first protein insertion in the absence of utilization of a pressure control method.

Factors that affect voltage-induced protein insertion into bilayer membranes are not well understood. High voltages are known to produce bilayer thinning and reversible bilayer defects but have not been shown previously to promote protein incorporation. Presented herein is a method that eliminates artifacts generated by bilayer thinning and reversible bilayer defects, and promotes the formation of robust bilayers. Described in the Examples section are investigations using GNMs. The robust nature of bilayers on GNMs allows measurement of voltage-induced insertions and maintaining a strong bilayer.

Also presented herein are methods for achieving stable insertions of proteins into lipid compositions (e.g., monolayers and/or bilayers) using voltage-induced protein insertion. Described in the Examples section are methods for voltage-induced incorporation of a bacterial porin (e.g., alpha-HL) into membrane bilayers, however, the voltage-induced protein insertion methods described herein also may be used with other aqueous proteins or detergent-solubilized proteins. Voltage-induced methods also can aid in the fusion of lipid vesicles with a PLB, and proteins incorporated into lipid vesicles can be incorporated into the PLB. Methods described herein can be used as a general purpose method to accelerate protein reconstitution into lipid compositions, including but not limited to, PLBs. In some embodiments, the insertion is a stable insertion of a single protein into a lipid bilayer. In certain embodiments, the insertion is a stable insertion of two or more proteins into a lipid bilayer. In some embodiments featuring insertion of two or more proteins, the two or more proteins are the same proteins, and in certain embodiments the two or more proteins are different proteins. Voltage-induced protein incorporation can also be used for the study of ion channels and porins in small area PLBs.

The methods described herein also can reduce the need for micromolar concentrations of proteins sometimes necessary to achieve protein insertion on lipid bilayers with smaller surface areas. The methods described herein also substantially reduce the time for successful insertion of protein into a lipid bilayer, especially when using protein solutions having lower concentrations. The methods described herein are particularly advantageous with proteins that are difficult to produce or isolate, or are unstable in the experimental system being utilized. Therefore, the methods described herein offer significant time and cost savings, while minimizing conditions that are detrimental to the lipid bilayers.

Nanopore Membrane Systems

A composition comprising one or more amphiphilic molecules that can form monolayers, bilayers or combinations thereof can be formed over, across or span an aperture of a channel in a membrane that is separating two fluid reservoirs, yielding an apparatus termed a "nanopore membrane system" or "nanopore membrane device" herein. The aperture can be nanometer or micrometer scale in diameter. Nanopore membrane systems offer some of the advantages described for supported lipid bilayers, and can be used in conjunction with monolayers, bilayers, combinations of monolayers and bilayers, and/or supported bilayers (e.g., supported lipid bilayers or spanning lipid bilayers). A device can be made with an amphiphilic molecule composition that is readily formed over the aperture or in the channel and has a relatively small surface area, which can give rise to favorable electrical characteristics.

Any suitable material can be utilized to generate nanopore membrane systems. A membrane of a device can be of a pure substance or a composite, or in some embodiments, comprises a coating that modifies a surface of the channel or nanopore structure. In some embodiments, a membrane system has a surface that comprises a hydrophobic substance. In certain embodiments, a membrane system has a surface that comprises a hydrophilic substance. In some embodiments, a membrane system has a surface that comprises hydrophobic and hydrophilic substances. In certain embodiments, a substrate may comprise a hydrophilic material (e.g., untreated glass), or it may be modified in a manner that renders one or more surfaces of the substrate (e.g., channel interior, channel exterior) hydrophilic (e.g. mildly hydrophilic, substantially hydrophilic).

Non-limiting examples of materials suitable for use in a nanopore membrane system, include glass, Si, $SiO_2$, $Si_3N_4$, alumina, nitrides, diamond, quartz, sapphire metals, ceramics, polymers (e.g., Teflon, polycarbonate) the like or combinations thereof. Non-limiting examples of types of glass suitable for generating nanopore membrane systems include fused silica glass, ninety-six percent silica glass, soda-lime silica glass, borosilicate glass, aluminosilicate glass, lead glass, doped glass comprising desired additives, functionalized glass comprising desired reactive groups, the like and combinations thereof. Non-limiting examples of minerals (e.g., quartz) suitable for generating nanopore membrane systems include quartz, tridymite, cristobalite, coesite, lechatelierite, stishovite and combinations thereof.

In certain embodiments, a substrate may be comprised of a hydrophobic material, such as Teflon, or it may be modified in a manner that renders one or more surfaces of the substrate (e.g., substrate channel interior, substrate channel exterior) hydrophobic (e.g. mildly hydrophobic, substantially hydrophobic). In some embodiments one or more surfaces of a substrate are coated with a hydrophobic substance, including without limitation an alkyl silane substance (e.g., 3-cyanopropyldimethylchlorosilane). Any suitable silane substance can be selected to render a substrate surface more hydrophobic and support interaction with lipids for formation of a lipid structure that spans the substrate aperture. In some embodiments, a spanning lipid structure contains a monolayer that interacts with an exterior surface of a substrate and a monolayer that interacts with an interior surface of the substrate, where the monolayers join together at about the edge of the opening of the aperture and form a lipid bilayer spanning the substrate aperture (e.g., U.S. Pat. No. 7,777,505, entitled "Nanopore platforms for ion channel recordings and single molecule detection and analysis," naming White et al. as inventors).

Membrane thickness often ranges from about 100 nanometers (nm) to 5 millimeters (mm) in thickness (e.g., about 100 nm, about 150 nm, about 200 nm, about 250 nm, about 300 nm, about 350 nm, about 400 nm, about 500 nm, about 600 nm, about 700 nm, about 800 nm, about 900 nm, about 1000 nm (e.g., about 1 µm), about 2 µm, about 3 µm, about 4 µm, about 5 µm, about 6 µm, about 7 µm, about 8 µm, about 9 µm, about 10 µm, about 15 µm, about 20 µm, about 25 µm, about 30 µm, about 35 µm, about 40 µm, about 45 µm, about 50 µm, about 60 µm, about 70 µm, about 80 µm, about 90 µm, 100 µm, about 110 µm, about 120 µm, about 130 µm, about 140 µm, about 150 µm, about 175 µm, about 200 µm, about 225 µm, about 250 µm, about 300 µm, about 350 µm, about 400 µm, about 450 µm, about 500 µm, about 600 µm, about 700 µm, about 800 µm, about 900 µm, 1000 µm (e.g. 1 mm), about 2 mm, about 3 mm, about 4 mm, or about 5 mm).

The diameter of an aperture of the channel in a membrane, across which an amphiphilic composition forms in a nanopore membrane system, often ranges in diameter from about 0.25 nanometers to about 50 µm (e.g., about 0.25 nanometers, about 0.5 nanometers, about 1 nanometer, about 1.5 nanometers, about 2 nanometers, about 2.5 nanometers, about 3 nanometers, about 3.5 nanometers, about 4 nanometers, about 4.5 nanometers, about 5 nanometers, about 6 nanometers, about 7 nanometers, about 8 nanometers, about 9 nanometers, about 10 nanometers, about 15 nanometers, about 20 nanometers, about 25 nanometers, about 30 nanometers, about 35 nanometers, about 40 nanometers, about 45 nanometers, about 50 nanometers, about 60 nanometers, about 70 nanometers, about 80 nanometers, about 90 nanometers, about 100 nanometers, about 125 nanometers, about 150 nanometers, about 175 nanometers, about 200 nanometers, about 250 nanometers, about 300 nanometers, about 350 nanometers, about 350 nanometers, about 400 nanometers, about 500 nanometers, about 600 nanometers, about 700 nanometers, about 800 nanometers, about 900 nanometers, about 1000 nanometers (e.g., 1 µm), about 1.5 µm, about 2 µm, about 2.5 µm, about 3 µm, about 3.5 µm, about 4 µm, about 5 µm, about 10 µm, about 15 µm, about 20 µm, about 25 µm, about 30 µm, about 35 µm, about 40 µm, about 45 µm, or about 50 µm). The channel formed in the membrane is of any suitable geometry, and sometimes has a substantially circular, oval, square, rectangular, rhomboid, parallelogram, or other like cross-section. The channel formed in the membrane is of any suitable profile, and sometimes has a substantially cylindrical or conical (e.g., tapering or expanding conical) profile. Nanopore membrane devices often are composed of a single conical-shaped channel or nanopore embedded in a suitable material. Membranes can be formed as known in the art and as described herein.

While a device often comprises a lipid composition traversing a substrate aperture, the composition traversing the substrate aperture may comprise any suitable amphiphilic molecule(s) or material(s) that can stably traverse an aperture and into which a protein can be incorporated (e.g., non-lipid substances). An amphiphilic molecule generally is composed of a hydrophobic portion and a polar portion. The terms "amphiphilic material" or "amphiphilic materials" refer to materials made of molecules having a polar, water-soluble group attached to a nonpolar, water-insoluble hydrocarbon chain. Amphiphilic materials sometimes can be polymers. Amphiphilic materials may be a pure substance or a mixture of different amphiphilic materials. The polymeric materials may be a polymer with a uniform molecular weight distribution, or a polymer with a non-uniform molecular weight distribution, or a mixture of polymers which comprise different monomers. Non-limiting examples of amphiphilic materials include lipids, detergents, surfactants, proteins, polysaccharides, and other chemical or biochemical materials that can be rendered amphiphilic.

The terms "detergent" or "detergents" as used herein refer to a surfactant or a mixture of surfactants. In some embodiments, "surfactant" or "surfactants" refer to any compound that (i) lowers the surface tension of a liquid, allowing easier spreading, and/or (ii) lowers the interfacial tension between two liquids, or between a liquid and a solid. Surfactants may act as: detergents, wetting agents, emulsifiers, foaming agents, and dispersants. Surfactants often are categorized as ionic (anionic or cationic), zwitterionic or amphoteric, or non-ionic. Non-limiting examples of surfactants include ammonium lauryl sulfate, sodium lauryl sulfate (SDS), sodium laureth sulfate (e.g., also known as sodium lauryl ether sulfate (SLES)), sodium myreth sulfate, dioctyl sodium sulfosuccinate, perfluorooctanesulfonate (PFOS), perfluorobutanesulfonate, alkyl benzene sulfonates, alkyl aryl ether phosphate, alkyl ether phosphate, fatty acid salts (e.g., soaps), sodium stearate, sodium lauroyl sarcosinate, perfluorononanoate, perfluorooctanoate, octenidine dihydrochloride, cetyl trimethylammonium bromide (CTAB), cetyl trimethylammonium chloride (CTAC), Cetylpyridinium chloride (CPC), polyethoxylated tallow amine (POEA), benzalkonium chloride (BAC), benzethonium chloride (BZT); 5-Bromo-5-nitro-1,3-dioxane, dimethyldioctadecylammonium chloride, dioctadecyldimethylammonium bromide, 3-[(3-Cholamidopropyl)dimethylammonio]-1-propanesulfonate (e.g., CHAPS), cocamidopropyl hydroxysultaine, amino acids, imino acids, cocamidopropyl betaine, lecithin, fatty alcohols (e.g., cetyl alcohol, stearyl alcohol, and the like), the like and combinations thereof.

A lipid molecule typically comprises at least one hydrophobic chain and at least one polar head. When exposed to an aqueous environment, lipids often will self assemble into structures that minimize the surface area exposed to a polar (e.g., aqueous) medium. Lipids sometimes assemble into structures having a single or monolayer of lipid enclosing a non-aqueous environment, and lipids sometimes assemble into structures comprising a bilayer enclosing an aqueous environment. In a monolayer structure, the polar portion of lipids (e.g., the head of the molecule in the case of phospholipids and other lipids commonly found in cell substrates) often is oriented towards the polar, aqueous environment, allowing the non-polar portion of the lipid to contact the non-polar environment.

A lipid bilayer typically comprises a sheet of lipids, generally two molecules thick, arranged so the hydrophilic phosphate heads point towards a hydrophilic aqueous environment on either side of the bilayer and the hydrophobic tails point towards the hydrophobic core of the bilayer. This arrangement results in two "leaflets" that are each a single molecular layer. Lipids self-assemble into a bilayer structure due to the hydrophobic effect and are held together entirely by non-covalent forces that do not involve formation of chemical bonds between individual molecules. Lipid bilayers generally also are impermeable to ions, which allow cells to regulate various processes that involve salt concentrations or gradients and intracellular pH by pumping ions across cell substrates using ion transport mechanisms.

In some embodiments, lipid bilayers are natural, and in certain embodiments lipid bilayers are artificially generated. Natural bilayers often are made mostly of phospholipids, which have a hydrophilic head and two hydrophobic tails (e.g., lipid tails), and form a two-layered sheet as noted above, when exposed to water or an aqueous environment. The center of this bilayer contains almost no water and also excludes molecules like sugars or salts that dissolve in water, but not in oil. Lipid tails also can affect lipid composition properties, by determining the phase of the bilayers, for example. A bilayer sometimes adopts a solid gel phase state at lower temperatures and undergoes a phase transition to a fluid state at higher temperatures. The packing of lipids within a bilayer also affects its mechanical properties, including its resistance to stretching and bending. Artificial bilayers (e.g., sometimes also referred to as "model lipid bilayers") are any bilayers assembled through artificial means, as opposed to bilayers that occur naturally (e.g., cell walls, lipid bilayers that cover various sub-cellular structures). An artificial bilayer can be made with synthetic and/or natural lipids, thus the process, not the material, defines an artificial or model system. Properties, such as stretching, bending or temperature induced phase transitions, have been studied with artificial model bilayers. The simplest model systems contain only a single pure synthetic lipid. The artificial bilayer also may contain a hydrophobic solvent, such as decane, hexadecane, pentane or other solvents and combinations thereof, that is used to disperse the lipid during bilayer formation and stabilize the formation of lipid bilayers across apertures in hydrophobic materials. The simplicity of a single lipid system is advantageous when determining physical or mechanical properties of bilayers. Model bilayers with greater physiological relevance can be generated utilizing mixtures of several synthetic lipids or, as mentioned, with natural lipids extracted from biological samples.

The presence of certain lipids or proteins sometimes can alter the surface chemistry of bilayers (e.g., viscosity or fluidity of lipid bilayers). Phospholipids with certain head groups can alter the surface chemistry of a bilayer. Non-limiting examples of bilayer constituents that can alter the surface chemistry of bilayers include fats, lecithin, cholesterol, proteins, phospholipids (e.g., phosphatidic acid (phosphatidate), phosphatidylethanolamine (e.g., cephalin), phosphatidylcholine (e.g., lecithin), phosphatidylserine, and phosphoinositides such as phosphatidylinositol (PI), phosphatidylinositol phosphate (PIP), phosphatidylinositol bisphosphate (PIP2) and phosphatidylinositol triphosphate (PIP3), phosphatidylglycerol, ceramide phosphorylcholine, ceramide phosphorylethanolamine, ceramide phosphorylglycerol), surfactants, the like and combinations thereof.

A device may include one or more types of molecules other than phospholipids. For example, cholesterol, which helps strengthen bilayers and decreases bilayer permeability can be included. Cholesterol also helps regulate the activity of certain integral substrate proteins. Different types or forms of lipid compositions (e.g., monolayers and/or bilayers) can be found naturally or generated artificially. Non-limiting examples of lipid compositions include monolayers (e.g., micelles) and bilayers including "black PLBs", vesicles (e.g., sometimes referred to as "liposomes"), supported lipid bilayers, linear lipid bilayers and the like.

A nanopore membrane device often comprises a lipid composition (e.g., monolayer, bilayer, combination thereof) over, across or spanning an aperture of a substrate. A lipid composition can comprise one or more types of lipids having various chain lengths and/or various structures of polar heads. A lipid composition of a nanopore membrane device often is relatively stable to mechanical disturbances, and can have a lifetime in excess of two weeks. A lipid composition sometimes comprises a lipid monolayer, sometimes comprises a lipid bilayer, and in some embodiments comprises a lipid layer that partially is a monolayer and partially is a bilayer. A portion of a lipid composition in a device can interact with one or more exterior and/or interior surfaces of a substrate. In some devices comprising both monolayer and bilayer lipid structures, solvent may be trapped at a location (i.e., annulus) between the substrate and the lipid layer at or near the monolayer and bilayer interface, which is addressed in greater detail hereafter. In certain embodiments, a lipid composition that spans across the substrate aperture is a combination of a lipid bilayer and monolayer. In various embodiments, a lipid monolayer deposited on the exterior surface of a substrate and a lipid monolayer deposited on the interior surface of the channel or nanopore that join together at about the edge of the channel or nanopore opening can form a lipid bilayer spanning or suspended across the aperture. The bilayer formed across an aperture sometimes is referred to as a "spanning lipid bilayer" herein.

In a spanning bilayer structure, a bilayer often is present across the substrate aperture and a monolayer is present on substrate surfaces (e.g., chemically modified surfaces and/or hydrophobic). In embodiments, a chemically modified device corrals a single protein pore in the lipid bilayer region that spans across the aperture. An inserted protein (e.g., protein pore, alpha hemolysin) often is able to diffuse in the bilayer across the aperture but often cannot leave this area to enter the lipid monolayer. Insertion of a sensing entity (e.g., protein pore) often occurs only in the bilayer region. A thin layer (e.g., about 1 to about 10 nm thick) containing solvent and ions sometimes is formed between a spanning lipid bilayer and one or more surfaces of the substrate. The thickness of this layer is defined as the distance between the exterior surface and the lipid bilayer and often plays a role in determining the resistance of the bilayer seal and the stability and fluidity of the bilayer. A spanning bilayer also sometimes includes an annulus formed between monolayers and a channel or nanopore surface, which can contain solvent (e.g., FIG. 15 of U.S. Pat. No. 7,777,505).

A protein often is inserted into a structure (e.g., monolayer and/or bilayer) formed by the lipid or amphiphilic material composition. A protein that is inserted into the structure can be water soluble, detergent-solubilized or incorporated into a lipid bilayer (e.g., vesicle, liposome) or a lipid monolayer (e.g., micelle) prior to insertion into a PLB, in some embodiments. Membrane proteins sometimes cannot be incorporated directly into the PLB during formation because immersion in an organic solvent sometimes can denature the protein. Exceptions include alpha hemolysin, MspA, and gramicidin. A membrane protein sometimes is solubilized with a detergent and added to the aqueous solution after the bilayer is formed. The dilution of the detergent stabilizing the protein forces the proteins to spontaneously insert into the bilayer over a period of minutes or hours, and often at a low frequency of success.

A vesicle is a lipid bilayer configured as a spherical shell enclosing a small amount of water or aqueous solution and separating it from the water or aqueous solution outside the vesicle. Because of the fundamental similarity to a cell wall, vesicles have been used to study the properties of lipid bilayers. Vesicles also are readily manufactured. A sample of dehydrated lipid spontaneously forms vesicles, when exposed to water. Spontaneously formed vesicles can be unilamelar (single-walled) or multilamellar (many-walled) and are of a wide range of sizes from tens of nanometers to several micrometers. A liposome is an artificially prepared vesicle, and also comprises a lipid bilayer and also can be made of naturally occurring or synthetic lipids, including phospholipids. There are four types of liposomes: MLV (multilamellar vesicles), SUV (Small Unilamellar Vesicles), LUV (Large Unilamellar Vesicles) and GUV (Giant Unilamellar Vesicles). Liposomes may be used to form PLBs on a surface or across apertures.

Voltage Bias and Voltage Toggling

The term voltage bias can refer to a particular voltage to perform a given operation. For example, a voltage bias can be an insertion voltage bias in some embodiments, and in certain embodiments, a voltage bias can be a measurement voltage bias. The term "insertion voltage bias" as used herein refers to a voltage that can be used to insert one or more proteins into a lipid bilayer. The term "measurement voltage bias" as used herein refers to a voltage that can be used to monitor the conductance of one or more proteins in the lipid bilayer.

In some embodiments, the measurement voltage bias facilitates the interaction of a ligand with a protein inserted in the lipid bilayer. In some embodiments, this interaction comprises the ligand translocating through the protein. In some embodiments, this interaction comprises the ligand binding within the protein without translocating through the protein. The interaction can be monitored by changes in current, impedance, hydrodynamic flow through the pore, the like or combinations thereof. An insertion voltage bias typically has a greater amplitude than a measurement voltage bias. In some embodiments, a measurement voltage bias is about 5 mV to about 450 mV (e.g., for measuring nucleic acid, about 50 mV to about 160 mV is utilized). A measurement voltage bias in certain embodiments is about 5 mV, about 10 mV, about 15 mV, about 20 mV, about 25 mV, about 30 mV, about 35 mV, about 40 mV, about 45 mV, about 50 mV, about 55 mV, about 60 mV, about 65 mV, about 70 mV, about 75 mV, about 80 mV, about 85 mV, about 90 mV, about 95 mV, about 100 mV, about 110 mV, about 120 mV, about 130 mV, about 140 mV, about 150 mV, about 160 mV, about 170 mV, about 180 mV, about 190 mV, about 200 mV, about 210 mV, about 220 mV, about 230 mV, about 240 mV, about 250 mV, about 260 mV, about 270 mV, about 280 mV, about 290 mV, about 300 mV, about 310 mV, about 320 mV, about 330 mV, about 340 mV, about 350 mV, about 360 mV, about 370 mV, about 380 mV, about 390 mV, about 400 mV, about 410 mV, about 420 mV, about 430 mV, about 440 mV, or about 450 mV.

The term "toggling" as used herein refers to application of two or more sequential voltage biases. The voltage biases may be of the same amplitude, and sometimes two or more voltage biases are of different amplitudes. In certain embodiments, the voltage biases are the same polarity, and sometimes the voltage biases have opposing polarities. The time between the application of two voltage biases may be the same during toggling, and sometimes one or more of the times is different during toggling. In some embodiments, voltage toggling comprises a first state to a second state, and in certain embodiments, the second state can be the same or different than the first state. Non-limiting examples of states that can be toggled between are: a resting voltage bias and a positive voltage bias, a resting voltage bias and a negative voltage bias, a positive voltage bias and a negative voltage bias, a positive voltage bias and a positive voltage bias, a negative voltage bias and a negative voltage bias, an insertion bias and an measurement bias, the like or combinations thereof.

In certain embodiments, the toggling can be cycled between states, where each state is a toggling step and each step can be repeated 1 or more times (e.g., 1 or more times, 2 or more times, 3 or more times, 4 or more times, 5 or more times, 10 or more times, 15 or more times, 20 or more times, 25 or more times, 30 or more times, up to 1,000,000 or more times), in succession or interspersed with other states. Non-limiting examples of toggling schemes include (i) resting state, insertion state; (ii) resting state, measurement state; (iii) resting state, insertion state, measurement state; (iv) resting state, insertion state (+), pore opening state (−); (v) resting state, insertion state (−), pore opening state (+); (vi) resting state, insertion state (+), resting state, insertion state (−); (vii) resting state, insertion state (+), insertion state (−), (viii) resting state, insertion state (+), measurement state; (ix) insertion state (−), measurement state; (x) insertion state (+), measurement state, insertion state (−); (xi) resting state, insertion state (+), resting state, insertion state (−), measurement state; (xii) resting state, insertion state (+), insertion state (−), measurement state; (xiii) resting state; (xiv) insertion bias state; (xv) measurement bias state; (xvi) pore opening state; (xvii) the like and combinations thereof.

In certain embodiments, the insertion voltage can be increased between toggling cycles. For example, during the first cycle an insertion voltage of 160 mV is applied followed by a measurement voltage of 120 mV and then an insertion voltage of −160 mV followed by a measurement voltage of 120 mV and then an insertion voltage of 200 mV followed by a measurement voltage of 120 mV.

In some embodiments, the voltage can be toggled to affect insertion of a protein into a PLB in a nanopore membrane system. In certain embodiments, the voltage can be toggled to open a closed, blocked or partially blocked protein pore already inserted into a nanopore membrane system. In some embodiments, the voltage is toggled from a resting state (e.g., about 0 mV) to a positive insertion bias (e.g., about +160 mV or greater (e.g., greater than +300 mV)). In certain embodiments, the voltage is toggled from a resting state to a negative insertion bias (e.g., about −160 mV or greater (e.g., greater than −300 mV)). In some embodiments, the voltage is toggled from an insertion bias (e.g., about +/−160 mV or greater) to a monitoring bias (e.g., about 120 mV). In certain embodiments, the measuring bias is a positive bias and in some embodiments, the measurement bias is a negative bias.

In certain embodiments featuring voltage toggling, the voltage can be toggled from a resting voltage to a positive pore opening voltage (e.g., about +350 mV). In some embodiments, the voltage can be toggled from a resting voltage to a negative pore opening voltage (e.g., about −350 mV). In some embodiments, the voltage toggling to open a pore can include multiple applications for voltage toggling, where the voltage is toggled between one or more independent states (e.g., resting state, insertion bias state, measurement bias state, pore opening state), and each state can be represented by a negative and/or positive voltage bias.

Proteins for Use in Voltage-Induced Protein Insertion Methods

Any suitable protein can be inserted into lipid compositions utilizing the voltage-induced insertion methods described herein. In some embodiments, proteins inserted into nanopore membrane systems described herein can range from about 50 amino acids to about 10,000 amino acids (e.g., about 60 amino acids, about 75 amino acids, about 100 amino acids, about 125 amino acids, about 150 amino acids, about 175 amino acids, about 200 amino acids, about 225 amino acids, about 250 amino acids, about 275 amino acids, about 300 amino acids, about 325 amino acids, about 350 amino acids, about 375 amino acids, about 400 amino acids, about 425 amino acids, about 450 amino acids, about 475 amino acids, about 500 amino acids, about 550 amino acids, about 600 amino acids, about 650 amino acids, about 700 amino acids, about 750 amino acids, about 800 amino acids, about 850 amino acids, about 900 amino acids, about 950 amino acids, about 1000 amino acids, about 1500 amino acids, about 2000 amino acids, about 2500 amino acids, about 3000 amino acids, about 3500 amino acids, about 4000 amino acids, about 4500 amino acids, about 5000 amino acids, about 6000 amino acids, about 7000 amino acids, about 8000 amino acids, about 9000 amino acids, or about 9500 amino acids).

In certain embodiments, a protein suitable for insertion using methods described herein, includes a region that can insert into a membrane or lipid composition. In some embodiments, a protein suitable for insertion using voltage induced protein insertion methods described herein includes a pore forming region that can insert completely into and through a cell membrane or lipid bilayer to allow passage of molecules from one compartment to another. In certain embodiments, a protein suitable for insertion using methods described herein permanently or reversibly binds to, or inserts partially into, a cell membrane or lipid composition and forms an association with, but does not insert completely through both layers of a bilayer. In some embodiments a protein suitable for insertion using methods described herein is a single subunit, and in certain embodiments, a protein suitable for insertion is multiple subunits.

In some embodiments, a protein suitable for use is post-translationally modified. In certain embodiments, the post-translational modification moiety is selected from an ubiquitin moiety, a phosphoryl moiety, an alkyl moiety (e.g., methyl), an alkanoyl moiety (e.g., acetyl), an alkanoic acid or alkanoate moiety (e.g., a fatty acid) or a glycosyl moiety.

In certain embodiments, a protein suitable for use is a native protein (e.g., a protein isolated and/or purified from it's native environment or synthetically produced using the genetic code for a wild type protein) or a modified version thereof (e.g., fusion protein, tagged protein, proteins modified to alter translational efficiency in a host organism, proteins modified to enhance functionality, functional proteins with 1, 2, 3 or more amino acid substitutions, additions, or deletions with respect to a native protein, the like or combinations thereof). In some embodiments, a protein suitable for use is a functional fragment of a native protein or modified version thereof.

In some embodiments, an inserted protein may comprise stable insertion of a single pass transmembrane protein (e.g., passes through the membrane only once) and in certain embodiments, an inserted protein may comprise stable insertion of a multi-pass transmembrane protein (e.g., passes through the membrane two or more times, due to the protein folding back on itself). In some embodiments, an inserted protein comprises an alpha helical transmembrane domain, and in certain embodiments, an inserted protein comprises a beta-barrel transmembrane domain. In some embodiments, an inserted protein comprises two or more inserted proteins of the same or different types.

In some embodiments, a protein suitable for insertion in a lipid composition can be used as a sensing entity and/or as a translocation entity. That is, a protein inserted into a lipid composition in conjunction with a nanopore membrane system can be used to (i) detect or monitor changes associated with the activity of the inserted protein, and/or (ii) act on a ligand (e.g., a nucleic acid (e.g., double stranded (ds) DNA, dsRNA, single stranded (ss) DNA, ssRNA), other proteins, virus particles, a cell type, an antibody, a binding pair (e.g., biotin-avidin and other binding pairs known to the user, that comprise at least one partner that can be associated with a lipid composition) the like or combinations thereof).

The sensing entity often is capable of recognizing an analyte of interest. Such a sensing entity may be able to interact with a nucleic acid in a mixture, a receptor for a hormone or small molecule messenger, an ion channel for an ion, an antigen for screening a library of antibodies, the like or combinations thereof, in certain embodiments. The sensing entity may serve as the conductivity channel, in some embodiments. The sensing entity may be an ion channel or other molecule-based conductive element engineered or modified to detect a specific chemical or biochemical analyte, or for sequencing nucleic acids, in certain embodiments.

Non-limiting examples of activities that can be detected or monitored include translocation, binding, modification (e.g., cleaving, addition of a moiety, removal of a moiety), the like or combinations thereof. In certain embodiments, the changes due to the activity can be measured by changes in voltage, current or resistance as measured using the nanopore membrane system. Non-limiting examples of ligands that can be sensed and/or translocated using proteins inserted into lipid compositions using methods described herein include nucleic acids (e.g., dsDNA, dsRNA, ssDNA, ssRNA), peptides, proteins, virus particles, specific cell types (e.g., based on the presence or absence of one or more specific cell surface markers or antigens), an antibody, a binding pair (e.g., antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, chemical reactive group/complementary chemical reactive group (e.g., sulfhydryl/maleimide, sulfhydryl/haloacetyl derivative, amine/isotriocyanate, amine/succinimidyl ester, and amine/sulfonyl halides) and the like.

Non-limiting examples of proteins suitable for insertion into lipid compositions to enhance the function of naturally derived or artificially generated lipid compositions are described herein and include, transporters, porin proteins (e.g., alpha-HL), cell surface antigens, antibodies, enzymes, extrinsic proteins (e.g., proteins associated with, but not embedded in a lipid composition), intrinsic proteins (e.g., transmembrane or integral membrane proteins) structural membrane-anchoring domains, peptide toxins, proteins involved in accumulation and transduction of energy, and proteins responsible for cell adhesion, the like, functional fragments thereof, or combinations of the foregoing.

Integral Membrane Proteins

Integral membrane proteins (IMP's) are proteins or an assembly of proteins that are found embedded in, and sometimes are permanently attached to, biological membranes. IMP's sometimes can only be dissociated from biological membranes by the use of detergents, non-polar solvents, or denaturing agents. IMP's frequently make up a substantial fraction of the protein encoded by an organism's genome. Integral membrane proteins typically only function when incorporated into a lipid bilayer.

Transmembrane proteins are a common type of IMP. Transmembrane proteins are sometimes referred to as integral polytopic proteins. Transmembrane proteins span the entire biological membrane, with domains that face the extracellular environment and/or the intracellular environment. Another type of IMP is an integral monotopic protein. Integral monotopic proteins are identified by being permanently attached to a membrane from one side, and require detergents for extraction or crystallization, even after removal of the transmembrane helices.

Because native bilayers often define the boundaries of the cell and its compartments, integral membrane proteins effect different intra- and inter-cellular signaling processes. Non-limiting examples of integral membrane proteins include, transporters, channels, receptors, enzymes, structural membrane-anchoring domains, proteins involved in accumulation and transduction of energy, and proteins responsible for cell adhesion.

Transmembrane proteins can be categorized by positioning of the amino terminal and carboxy terminal domains and/or by the three-dimensional conformation of the protein or parts of the protein. Transmembrane protein types I, II, and III are single pass molecules (e.g., pass through the lipid bilayer only once), while type IV transmembrane proteins are multiple pass molecules (e.g., pass through the lipid bilayer more than once). Type I transmembrane proteins are anchored to the lipid membrane with a stop-transfer anchor sequence and have their N-terminal domains targeted to the ER lumen during synthesis (and the extracellular space, if mature forms are located on plasmalemma). Type II and III transmembrane proteins are anchored with a signal-anchor sequence, with type II being targeted to the ER lumen via the C-terminal domain, and type III having the N-terminal domain targeted to the ER lumen. Type IV transmembrane proteins are subdivided into IV-A, with the N-terminal domain targeted to the cytosol, and IV-B, with the N-terminal domain targeted to the lumen.

As noted above, transmembrane proteins also can be characterized by their three-dimensional conformation. Transmembrane proteins usually assume in part or in whole, (i) an alpha helical conformation, or (ii) a beta-barrel conformation.

Alpha helical transmembrane proteins often are found in the inner membrane of bacterial cells and the plasma membrane of eukaryotic cells, and less frequently in the outer membranes of eukaryotes. Alpha helical transmembrane proteins make up the majority of transmembrane proteins, with as much as 27% of all human proteins falling into the alpha helical transmembrane protein category.

Beta-barrel proteins are less widely distributed in cell membranes, and are found in outer membranes of Gram-negative bacteria, cell wall of Gram-positive bacteria, and outer membranes of mitochondria and chloroplasts. Substantially all beta-barrel transmembrane proteins have a simple up-and-down topology, which may reflect their common evolutionary origin and similar folding mechanism.

Non-limiting examples of transmembrane proteins include rhodopsin (e.g., from vertebrates) and rhodopsin like proteins (e.g., from archaebacteria and halobacteria), light reaction centers and/or photosystems I and II (e.g., from all green plants, algae and many bacteria), cytochrome c oxidases (e.g., from bacteria and mitochondria), glycerol-3-phosphate transporter (e.g., found in most organisms), lactose permease (e.g., found in most organisms), T-cell receptor transmembrane dimerization domain (e.g., from homo sapiens), cytochrome P450 oxidases (e.g., found in all organisms), virulence related outer membrane proteins (e.g., from most gram negative bacteria including *Salmonella typhimurium, E. coli,* and *Yersinia enterocolitica*), nucleoside specific porin (e.g., from *E. coli* and other bacteria), MspA porin (e.g., from *Mycobacterium smegmatis*), and alpha hemolysin (e.g., from *Staphylococcus Aureus*).

Porin Proteins

Porin proteins are proteins that fall into the beta-barrel class of transmembrane proteins. Porins act as a pore or channel through which molecules can diffuse. Unlike other membrane transport proteins, porins are large enough to allow passive diffusion. Porins typically control the diffusion of small metabolites, like sugars, ions, amino acids and the like. Porins sometimes are chemically selective. A particular porin sometimes transports only one group of molecules, and sometimes a porin is specific for only one molecule.

Porins typically are composed of beta sheets, which in turn, generally are linked together by beta turns on the cytoplasmic side and long loops of amino acids on the other side. The beta sheets lie in an anti-parallel fashion and form a cylindrical tube, called a beta barrel. The amino acid composition of the porin beta sheets is unique in that polar and nonpolar residues alternate along the beta sheets. This arrangement results in a conformation in which most or all of the nonpolar residues typically face outward so as to interact with the nonpolar lipid membrane, and most or all of the polar residues typically face inwards into the center of the beta barrel to interact with the aqueous channel.

Non-limiting examples of porin proteins include aquaporins (e.g., from mammals and plants), maltoporins and other sugar specific porins (e.g., from gram negative bacteria (e.g., *E. coli, S. typhimurium,* and other bacteria), OmpG porin (e.g., gram negative bacteria), opacity porins (e.g., from *Neisseria* bacteria), nucleoside specific porin (e.g., from *E. coli* and other bacteria), MspA porin (e.g., from *Mycobacterium smegmatis*), gramicidin (e.g., *Bacillis brevis*), and alpha hemolysin (e.g., from *Staphylococcus Aureus*).

Hemolysins and Alpha-Hemolysin

Hemolysins are exotoxins produced by bacteria that cause lysis of red blood cells in vitro or in vivo. Visualization of hemolysis of red blood cells in agar plates facilitates the categorization of some pathogenic bacteria such as *Streptococcus* and *Staphylococcus*. Although the lytic activity of some hemolysins on red blood cells may be important for nutrient acquisition or for causing certain conditions such as anemia, many hemolysin-producing pathogens do not cause significant lysis of red blood cells during infection. Although hemolysins are able to lyse red blood cells in vivo, the ability of hemolysins to target other cells, including white blood cells, often accounts for the effects of hemolysins in the host. Many hemolysins are pore forming proteins.

A non-limiting example of a porin protein useful for insertion into lipid bilayers is alpha-HL, sometimes also referred to as alpha toxin. Alpha-hemolysin (e.g., alpha-HL) forms a heptameric beta-barrel in biological membranes. Alpha-HL is secreted as a monomer that binds to the outer membrane of susceptible cells. Upon binding, the monomers oligomerize to form a water-filled transmembrane channel that facilitates uncontrolled permeation of water, ions, and small organic molecules. Rapid discharge of vital molecules, such as ATP, dissipation of the membrane potential and ionic gradients, and irreversible osmotic swelling leading to rupture or lysis of the cell wall, frequently causing death of the host cell. This pore-forming property has been identified as a major mechanism by which protein toxins cause damage to cells.

Several properties of alpha-HL make this membrane channel suitable for various biotechnological applications: assembled alpha-HL is stable over a wide range of pH and temperature, its transmembrane pore stays open at normal conditions, alpha-HL can insert into to various biological or synthetic lipid bilayers, the insertion proceeds spontaneously and does not require specific ionic conditions. Alpha-HL inserted into a lipid bilayer may prove useful as delivery systems, as a component of a stochastic sensor, and transporters or translocators. Alpha-HL has been shown to have the ability to translocate nucleic acids through the pore formed in a lipid bilayer.

Non-limiting examples of pore forming hemolysins include listeriolysin O (e.g., from *Listeria monocytogenes*), alpha toxin or alpha hemolysin (e.g., from *Staphylococcus aureus*), PVL cytotoxin (e.g., from *Staphylococcus aureus*), and cytolysin A (e.g., from *E. coli*).

Provided in the examples are the amino acid and nucleotide sequences identification numbers (e.g., SEQ ID NOS:) for the native and modified alpha hemolysin described herein. In some embodiments, a protein suitable for insertion into a lipid composition using methods described herein is encoded by a nucleotide sequence identical to SEQ ID NOS: 3 and 4. In certain embodiments, a protein suitable for insertion into a lipid composition using methods described herein has an amino acid sequence identical to, or containing 1, 2, or 3 amino acid changes with respect to an amino acid sequence of SEQ ID NOS: 1 and 2.

Methods of Use

In certain embodiments, provided is a method for detecting an analyte or a method for analyzing interactions between a sensing entity and an analyte, comprising: contacting a solution suspected of containing an analyte of interest with a nanopore device including a sensing entity that recognizes the analyte in association with a membrane in contact with a channel in the nanopore system, where the sensing entity is inserted in the membrane by a method described herein; applying a voltage across the membrane; and analyzing the electrical conductivity to determine the presence, absence or amount (e.g., concentration) of the analyte of interest in the sample. The analyte may be any entity that is recognizable by the sensing entity. Non-limiting examples of analytes include chemical or biological molecules, ions, polymers, lipids, particles, nucleic acids the like or combinations thereof.

In some embodiments, the biomolecule is a nucleic acid, such as deoxyribonucleic acid (DNA) or ribonucleic acid (RNA). In some embodiments, provided are methods for sensing a nucleic acid in a sample, or sequencing sequential nucleotide bases in the nucleic acid, comprising: contacting a solution suspected of containing a nucleic acid of interest with a nanopore device that includes a sensing entity that recognizes the nucleic acid in association with a membrane in contact with a channel in the nanopore system, where the sensing entity is inserted in the membrane by a method described herein; applying a voltage across the membrane; and analyzing the electrical conductivity to determine the presence, absence or amount (e.g., concentration) of the nucleic acid, or sequence of sequential bases in the nucleic acid in the sample. In some embodiments, the nucleic acid passes through a channel in the protein, and the electrical conductivity can change as separate bases of the nucleic acid pass through the channel.

When the sensing entity binds to the analyte, the binding event often causes a change in current (e.g., an increase in current or reduction in current) across the sensing entity. The current detected through the sensing entity can be measured using alternating current (AC) and/or direct current (DC) measurements. In certain embodiments, a modified glass nanopore system comprises a single protein ion channel as a sensing entity, for instance, alpha-HL, in the lipid bilayer region that spans the glass channel or nanopore opening. The bilayer structure spanning the modified glass channel or nanopore typically is configured such that current can flow through the protein channel (e.g., current flows only through the channel). When an analyte is recognized by the channel and/or passes through ("translocates") the channel, it often partially blocks ionic current through the pore. The channel blockage often is measured by a transient increase in ionic resistance (or decrease in ionic current), in some embodiments. In certain embodiments, the concentration of an analyte and/or the binding affinity of an analyte can be measured by "sensing" the binding rate of the analyte.

EXAMPLES

The examples set forth below illustrate certain embodiments and do not limit the technology.

Example 1

Materials and Methods

Described below are the results of experiments performed to develop a method of controlling the insertions of proteins, in particular alpha-HL, into PLBs. Application of a relatively high insertion voltage of between about 160 mV to about 2000 mV across the bilayer, significantly enhances incorporation of protein channels, allowing low concentrations of proteins to be used. The voltage induced protein insertion method described herein has the added advantageous benefit that subsequent insertions can be almost completely avoided after the voltage is reduced below the insertion voltage, typically below 160 mV.

Apparatus

Glass nanopore membranes (GNMs) were fabricated, the interior of the GNM was filled with an electrolyte solution (e.g., 1 M NaCl (Sigma), 10 mM Tris, 2 mM EDTA and pH 7.2) and inserted horizontally through the wall of a polycarbonate cell into a fluid reservoir. An Ag/AgCl electrode produced by treating a 0.25 mm Ag wire with household bleach was placed interior to the GNM. A pipette holder (DAGAN, HB120) provided a secure mounting for the GNM, Ag/AgCl electrode interior to the GNM and provided a means of maintaining a constant back pressure on the GNM. The test cell had a reservoir of 250 µL and ports connected to syringes to allow for raising and lowering the fluid level in the reservoir. A second Ag/AgCl electrode was placed in the test cell reservoir. The GNM electrode and reference electrode were connected to a custom resistive feedback headstage that allows for applying a voltage bias between the electrodes and provides a low noise readout of the current between the two electrodes. All voltages were referenced with respect to the electrode in the GNM. For example, a negative bias indicates that the test cell reservoir electrode is at a negative potential with respect to the electrode interior to the GNM. Data was acquired with a PCI-6251 (National Instruments) DAQ card in a personal computer (Dell). A custom LabView application handled voltage control, data acquisition, and simple signal processing such as filtering.

Bilayer Formation 1,2-diphytanoyl-sn-glycero-3-phosphocholine (DPhPC) (Avanti) was diluted in decane (Sigma) to a concentration of 5 mg/ml. A test cell reservoir was filled to a level just above the face of the GNM with the electrolyte solution described herein. Diethylene Triamine Penta (methylene phosphoric acid) (DTPMPA; Sigma) was present at a concentration of 500 nM, in some experiments. A small drop (e.g., less than about 0.5 µL) of the lipid/decane mixture was added to the surface of electrolyte. The fluid level in the test cell reservoir was then lowered below the face of the GNM and then raised above the face of the GNM. This action typically resulted in a bilayer although in some cases additional lipid was added and the raising and lowering repeated.

Protein Pore Preparation

Both monomeric and heptameric forms of the alpha-HL protein were used in experiments described herein. A monomeric type of wild-type (WT) alpha-HL from List Laboratories was used in some experiments. In addition, monomeric and heptameric modified versions of alpha-HL with lysine (K) substituted for methionine (M) at residue 113 were used in additional experiments. This modification is termed $(M113K)_7$, where the 7 indicates that all monomers in the alpha-HL heptamer have the same M113K modification.

Wild-Type Alpha Hemolysin (Alpha-HL)

Wild-type alpha-HL was obtained from List Biological Laboratories (Campbell, Calif.). The lyophilized powder was diluted with 18.2 megaohm water to a concentration of 1 mg/mL and stored at −80° C. About 0.3 µL of the WT alpha-HL was added to the test cell for a final concentration of about 45 nM. The amino acid and nucleotide sequences of the wild-type alpha-HL utilized in embodiments described herein are presented in Example 5 as SEQ ID NOS: 1 and 3, respectively.

Modified Heptameric Alpha Hemolysin (Alpha-HL)

Mutant alpha-HL genes coding for the M113K modification were constructed by site-directed mutagenesis (Mutagenex, Piscataway, N.J.) of a WT alpha-HL gene35 in a T7 vector (pT7-αHL). M113K monomers were synthesized by coupled in vitro transcription and translation (IVTT) using an *E. coli* T7 S30 Extract System for Circular DNA from Promega (Madison, Wis.). Monomers were assembled into heptamers by incubation with rabbit blood cell membranes for 1-2 hours. The resulting heptamers were purified by SDSpolyacrylamide gel electrophoresis, concentrated to 5 nM, and stored in aliquots at −80° C. The resulting IVTT protein was diluted by about 10 fold prior to addition to the test cell. About 2 µL of purified and concentrated heptamers typically was added to the test cell for a final concentration of 5 pM. The amino acid and nucleotide sequences of the modified alpha-HL utilized in embodiments described herein are presented in Example 5 as SEQ ID NOS: 2 and 4, respectively.

Modified Monomeric Alpha-HL

The monomeric form of the mutant alpha-HL M113K was expressed by Paragon BioServices using an *E. Coli* BL21 culture. Plasmids encoding the M113K mutant of alpha-HL were incorporated into *E. Coli* BL21 for expression. Cells were grown in LB medium and the culture was induced with 1 mM IPTG for expression. After three hours, cells were harvested by centrifugation and stored at −20° C. The resulting cell paste was lysed using a microfluidizer and clarified by centrifugation. Clarified lysate was brought to 75% saturation with Ammonium Sulfate to precipitate the protein. After one hour at 4° C., precipitated protein was collected by centrifugation and resuspended in a 10 mM Na-Acetate buffer (pH 5.0) with 20 mM NaCl. Solubilized material was then clarified by centrifugation and loaded onto a SP-Sepharose column. Bound protein was washed and then eluted using a linear NaCl gradient (0 to 500 mM). Pooled fractions containing the protein were then concentrated and further purified via size exclusion chromatography. This mutant also has the K8A modification that reduces the protease sensitivity of the pore.

Oligonucleotides

Stock solutions (e.g., 100 µM) of PAGE purified homo-poly(dT)$_{100}$ (SEQ ID NO: 5) oligonucleotides (Sigma) were prepared in 10 mM Tris 1 mM EDTA. Approximately 4 µL of stock solution was added to the test cell reservoir to achieve a final concentration of about 2 µM.

Example 2

High Voltage Insertions

Previous attempts at incorporating heptameric alpha-HL produced by in vitro transcription/translation (IVTT) methods into lipid bilayers on GNMs did not result in success. Many trials were attempted over a wide range of dilutions without obtaining a single insertion into DPhPC bilayers. The conclusion drawn by many investigators at the time was that the small area of the bilayer limited insertion. For example, a 1 µm diameter bilayer on a GNM has an area that is 22,000 fold smaller than the typical 150 µm diameter bilayers. As typical single insertions of alpha-HL occur within ~30 minutes under normal conditions when using a 150 µm bilayer, the insertion time on the small aperture GNM would be on the order of weeks. Although bilayer lifetimes of 400 hours have been reported for GNMs, it is not practical to have such long waiting times to obtain a single insertion.

Described herein are high voltage induced protein insertions. In these experiments, an increasing voltage (e.g., up to 500 mV) was applied across a bilayer. An increased rate of protein insertion was observed at the highest voltages.

Two effects are seen as the voltage is stepped from a low voltage to a high voltage: (1) a change in DC bias produces a large transient increase in current amplitude, due, in part, to the AC conductance of the systems capacitance, and (2) the baseline current measured across the bilayer increases due to the small but measurable conductance of the bilayer and platform. Both effects are shown in FIG. 1. Shown in FIG. 1 is the effect of stepping the voltage, on a bilayer (PLB) formed on a GNM, in discrete 10 mV increments from 230 mV to 350 mV. Large spikes in current are measured when the voltage is changed due to charging of the bilayer and GNM capacitance. The oscillations in the baseline are due to electrical interference in the measurement. The data presented in FIG. 1 is low pass filtered at 100 Hz.

Figure 2:
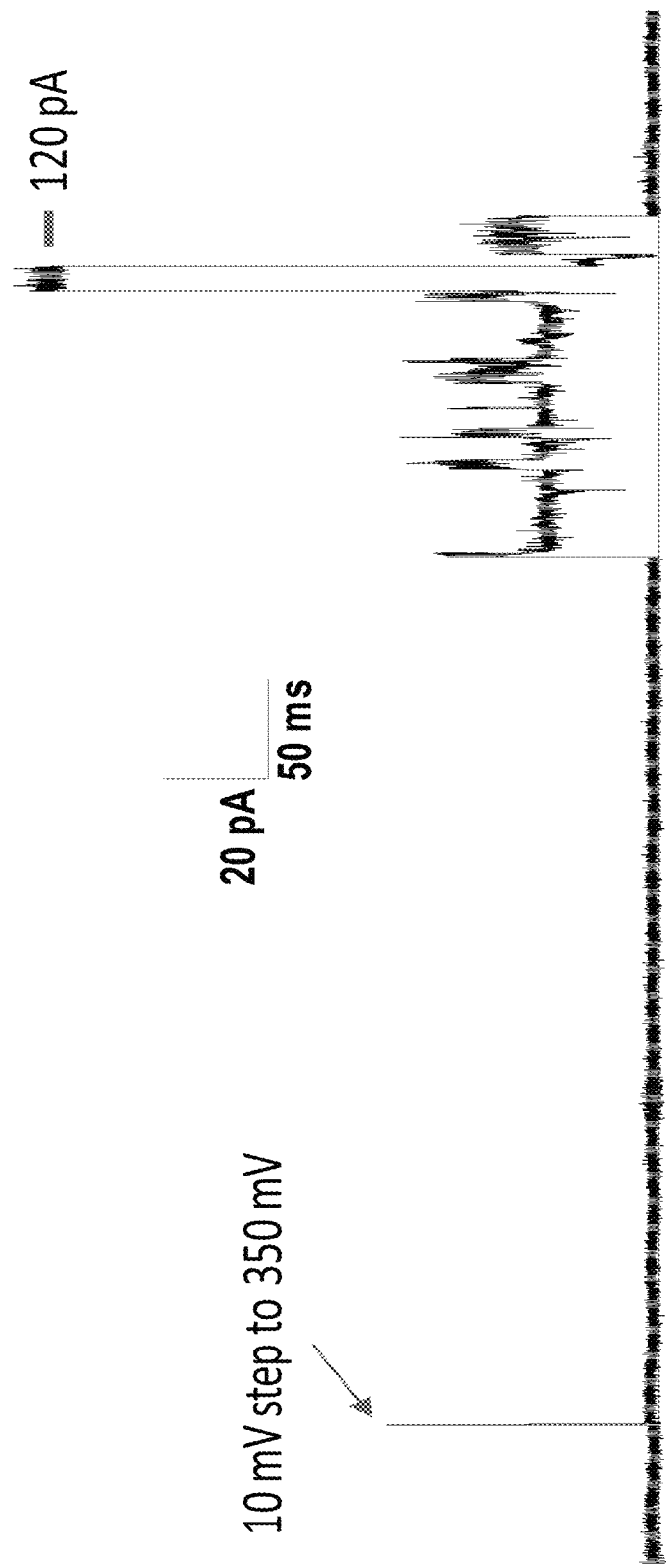
FIG. 2 graphically illustrates the results of voltage-induced insertion of wild type alpha-hemolysin (HL) approximately 500 ms after increasing bias voltage to 350 mV. Experimental details and results are described in Example 2.

Approximately 500 ms after the step to 350 mV, the measured current spikes to about 120 pA, the expected value for an open pore current for alpha-HL at this bias in 1M NaCl (pH 7.1), as shown in FIG. 2. Shown in FIG. 2 are the results of voltage-induced insertion of monomeric WT alpha-HL described herein, approximately 500 milliseconds (ms) after increasing voltage bias to 350 mV. As seen in FIG. 2, the current does not remain steady at this point of the insertion, switching between a number of discrete conductance levels. This phenomena may be caused by a partially blocked protein insertion and was observed frequently when using high voltages to induce protein insertions. The key indicator that an insertion had been achieved was the presence of a short lived, stable current at the expected open pore current of alpha-HL.

Figure 3:
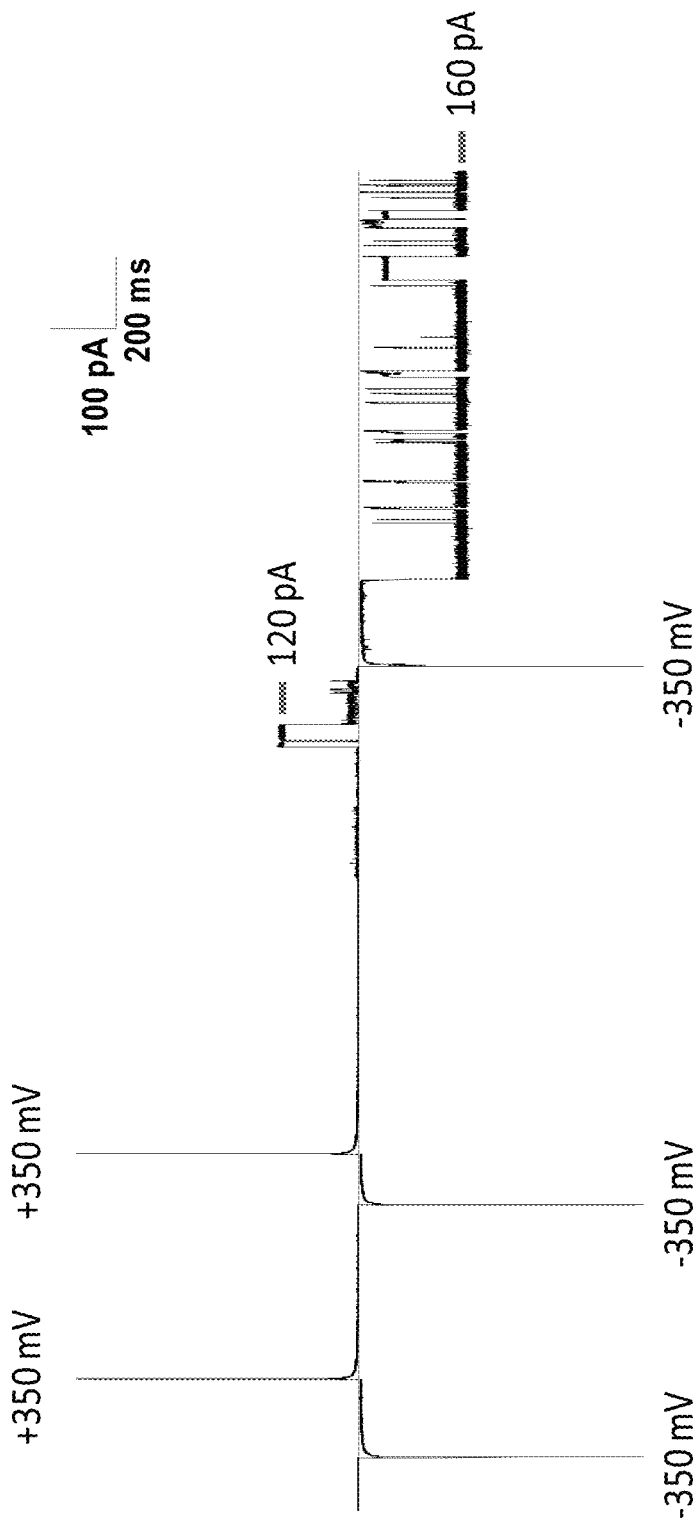
FIG. 3 graphically illustrates the results of voltage toggling insert and then open an inserted pore. Experimental details and results are described in Example 2.

To open the pore, the voltage was quickly toggled between ±350 mV. The pore remains open after toggling 5 times over a period of about 2.5 s, as shown in FIG. 3. FIG. 3 illustrates the results of voltage toggling to open an inserted pore complex. Rapidly switching the voltage between +350 mV and −350 mV, causes the protein pore to open. Short blockades of the open pore, seen as vertical spikes from the −160 pA current, are caused by the translocation of poly(dT)$_{100}$ (SEQ ID NO: 5). The large, transient current spikes are created by the 700 mV change in bias required to go from −350 mV to +350 mV.

The difference between the open channel current at positive and negative bias (e.g., 120 pA vs −160 pA) is due to the rectification of the alpha-HL pore. A homo-oligonucleotide poly(dT)$_{100}$ was present in the test cell reservoir and readily translocates the alpha-HL pore when the bias is negative. The characteristic blocking level and event direction for the poly(dT)$_{100}$ (SEQ ID NO: 5) serves as a positive indicator that the wild-type alpha-HL protein has properly inserted into the bilayer. After insertion, the voltage can be reduced to the desired operating level.

High Voltage Insertion Method

Figure 4:
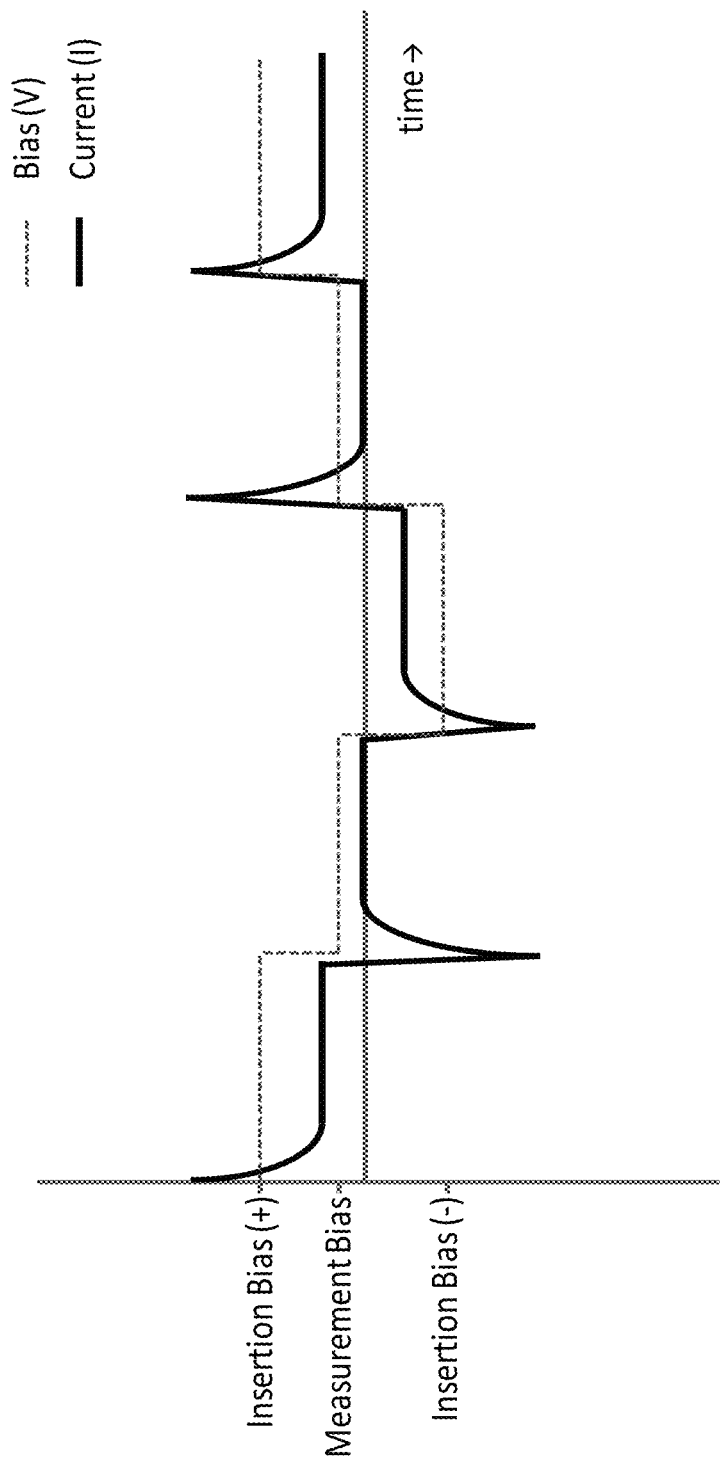
FIG. 4 graphically illustrates the voltage toggling scheme for inducing protein insertions and automatically checking for open pores using the voltage induced protein insertion method described herein. Details of the method are described in Example 2.

An initial pore insertion sometimes can be clogged or blocked, therefore an automated method for pore insertion and pore opening was developed, using voltage toggling. In this method, the bias voltage is set to the desired level to promote insertion for a fixed period of time. The voltage is then reduced to the desired measurement bias, typically lower than the insertion bias, and the presence or absence of a single insertion is determined. Using a lower bias to determine the presence or absence of the protein insertion is desirable in many cases as the open pore current at the insertion bias may saturate the measurement electronics making it difficult to discriminate between a protein insertion and a bilayer failure. If no protein insertion is measured the bias is then switched to an equal but opposite insertion bias. This is then followed after a short time by a switch to the measurement bias. The process is repeated until a single insertion is measured. The method is illustrated in FIG. 4 and illustrates the voltage toggling scheme used to induce protein insertions and automatically check for open pores.

The voltage toggling method can be performed with positive insertion bias only, negative insertion bias only, or positive and negative insertion bias. In addition, the insertion bias can be set at a constant value or steadily increased until an insertion is observed.

Example 3

Measuring the Rate of Protein Insertion—Monomeric Mutant Alpha-HL

Figure 5:
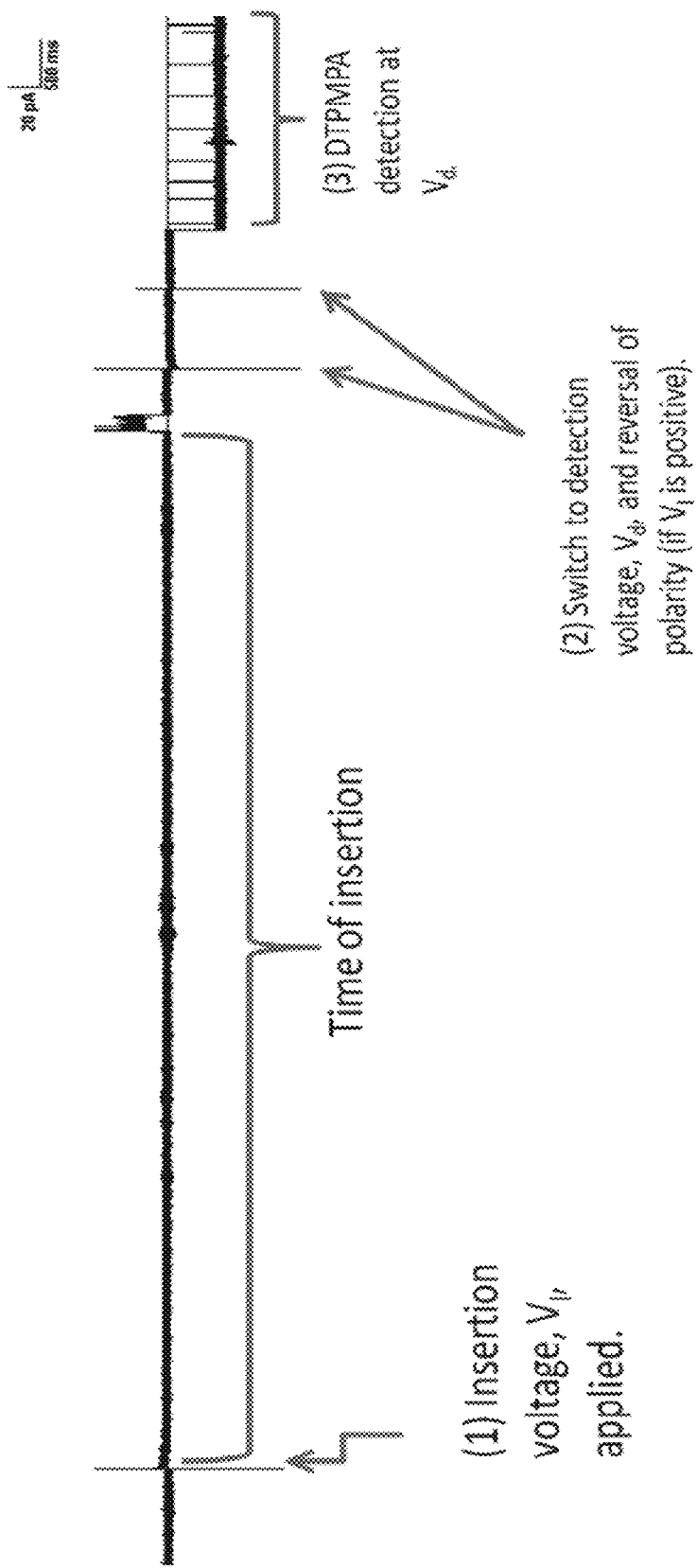
FIG. 5 graphically illustrates the timing of an alpha-HL incorporation event into a PLB under a constant bias. Experimental details and results are described in Example 3.

The insertion rate of monomeric M113K alpha-HL was investigated as a function of the applied voltage. Voltage bias was held at a constant level and the time for an insertion event was measured. All measurements were performed using a constant back pressure of 120 mmHg and a 35 nM solution of monomeric M113K alpha-HL. Immediately after adding the alpha-HL to the test cell, the voltage was set to a fixed level. The current was then monitored for any sudden increases or spikes, which indicate an insertion of alpha-HL into the bilayers. Upon insertion, the pore frequently becomes blocked immediately, which can be alleviated by toggling the sign of the applied voltage (e.g., positive or negative applied voltage) a few times to cause pore opening. If diethylenetriamine penta(methylene phosphonic acid) (DTPMPA) blocking events are detected after initial indication of an insertion event, the insertion event is verified. If DTPMPA blocking events are not detected after initial indication of an insertion event, the event is ignored and the bias is increased to the insertion voltage. FIG. 5 illustrates the timing of an alpha-HL incorporation even into a PLB under a constant bias. Insertion is identified by a sudden jump in current, and then verified by toggling the voltage and detection of characteristic blockades by DTPMPA. The results presented in FIG. 5, were obtained utilizing continuous data acquisition at a 50 kHz sampling rate. The data illustrate an insertion voltage was applied until there was an irreversible change in the signal.

Each trial was repeated at least 10 times for both positive and negative applied voltages, using a voltage magnitude in the range of about 280 mV to about 380 mV. The data for the individual trials and best fit curves for the mean and standard error of the time-to-insertion for both positive and negative voltages are displayed in FIGS. 6A and 6B. FIGS. 6A and 6B graphically illustrate the voltage dependence of mean time for insertion of alpha-HL into a PLBs, using a 35 nM monomeric alpha-HL solution. In both positive voltage and negative voltage cases, the time to insertion shows an exponential dependence on the insertion voltage. The best fit curves predict that at −120 mV the mean time-to-insertion is about 4868 seconds, or 81.13 minutes. This is consistent with anecdotal evidence and generally would be considered too long to wait for a protein insertion event.

Figure 7:
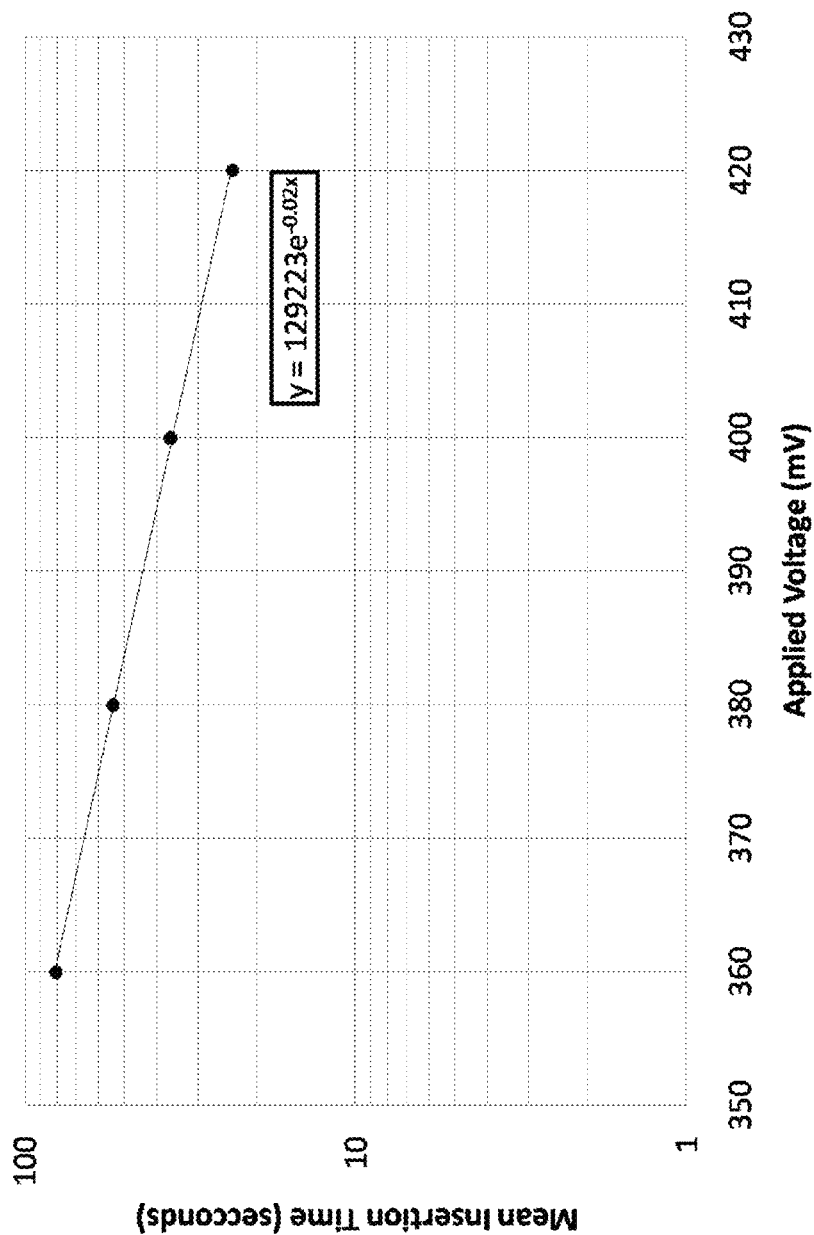
FIG. 7 graphically illustrates the voltage dependence of mean time to insertion of alpha-HL into a PLB using a 17.5 nM monomeric alpha-HL solution. Experimental details and results are described in Example 3.

Investigation of the rate of protein insertion was also carried out utilizing a 50% reduced concentration of the alpha-HL monomer (17.5 nM). The results obtained were consistent with the results obtained at 35 nM alpha-HL monomer; an exponential relationship between the inverse of the applied voltage and time to insertion, as shown in FIG. 7. FIG. 7 graphically illustrates the voltage dependence of mean time to insertion of alpha-HL into a PLB using a 17.5 nM monomeric alpha-HL solution. The exponential factor at an alpha-HL concentration of 17.5 nM is roughly a factor of 2 lower than that seen at 35 nM (e.g., see y values in graphs in FIGS. 6A, 6B and 7; −0.02 vs. −0.035), the same factor by which the monomer concentration differs in between the two experiments. The intercept at zero bias is reduced by greater than 80%, the opposite of what would be expected for a reduction in monomer concentration.

Example 4

Discussion and Conclusions

The effect of voltage on the insertion rate of protein channels into PLBs sometimes is pronounced. An increase in bias from 280 mV to 380 mV produces a 30 fold reduction in the mean time to insertion for a 35 nM solution of monomeric alpha-HL, as shown in FIGS. 6A and 6B. Protein insertion holding voltages typically are closer to 100 mV, and would yield a mean time for insertion of approximately 5.5 hours. Due to difficulties in preparing for and performing PLB measurements, an average time for insertion of over 5 hours would make performing any experiments difficult, if not eliminating the ability to perform them completely. By reducing the time to insertion to a few minutes or even seconds, the high voltage protein insertion method described herein makes it possible to investigate the properties of bilayer spanning proteins at low concentrations.

The incorporation of alpha-HL into a PLB effectively represents a single molecular event. A likely mechanism involves pre-formation of the heptamer on the surface of the bilayers, prior to insertion in the bilayer. Once the pore inserts into the bilayer, it becomes quite stable, although alpha-HL pores can be removed from bilayers on GNMs using negative back pressure, as shown by White et al.

Assuming that the pore insertion represents a thermally activated stochastic event, the times to first insertion should be exponentially distributed as;

$$P(t) = \frac{1}{\tau} e^{-t/\tau}, \qquad \text{equation 1,}$$

where $\tau$ is the characteristic time to insertion. The mean time to insertion can be related to the amount of time that must be given to provide a ~95% probability that a single insertion will occur, utilizing equation 1. The mean time to insertion is given by $$\bar{\tau} = \tau \ln 2 \qquad \text{equation 2.}$$

The time necessary to have a 95% confidence that a single insertion will occur is then given by $$\tau_{95} \approx 2\bar{\tau} \qquad \text{equation 3.}$$

Therefore, at a bias of 100 mV, a typical insertion holding voltage, it would be necessary to wait over 11 hours to have at least a 95% confidence that a protein insertion occurred, utilizing a 35 nM alpha-HL solution, as described in the experiments presented in Example 2.

Viewed alternatively, when assessing whether a particular trial is a success or failure, adjusting the voltage to 380 mV, as shown in FIGS. 6A and 6B, affords the user a small chance of failure and a wait of only 10 minutes for 95% confidence of occurrence of a protein insertion event, whereas there is only a 2% chance of successful protein insertion event at the 100 mV bias within 10 minutes.

Figure 8:
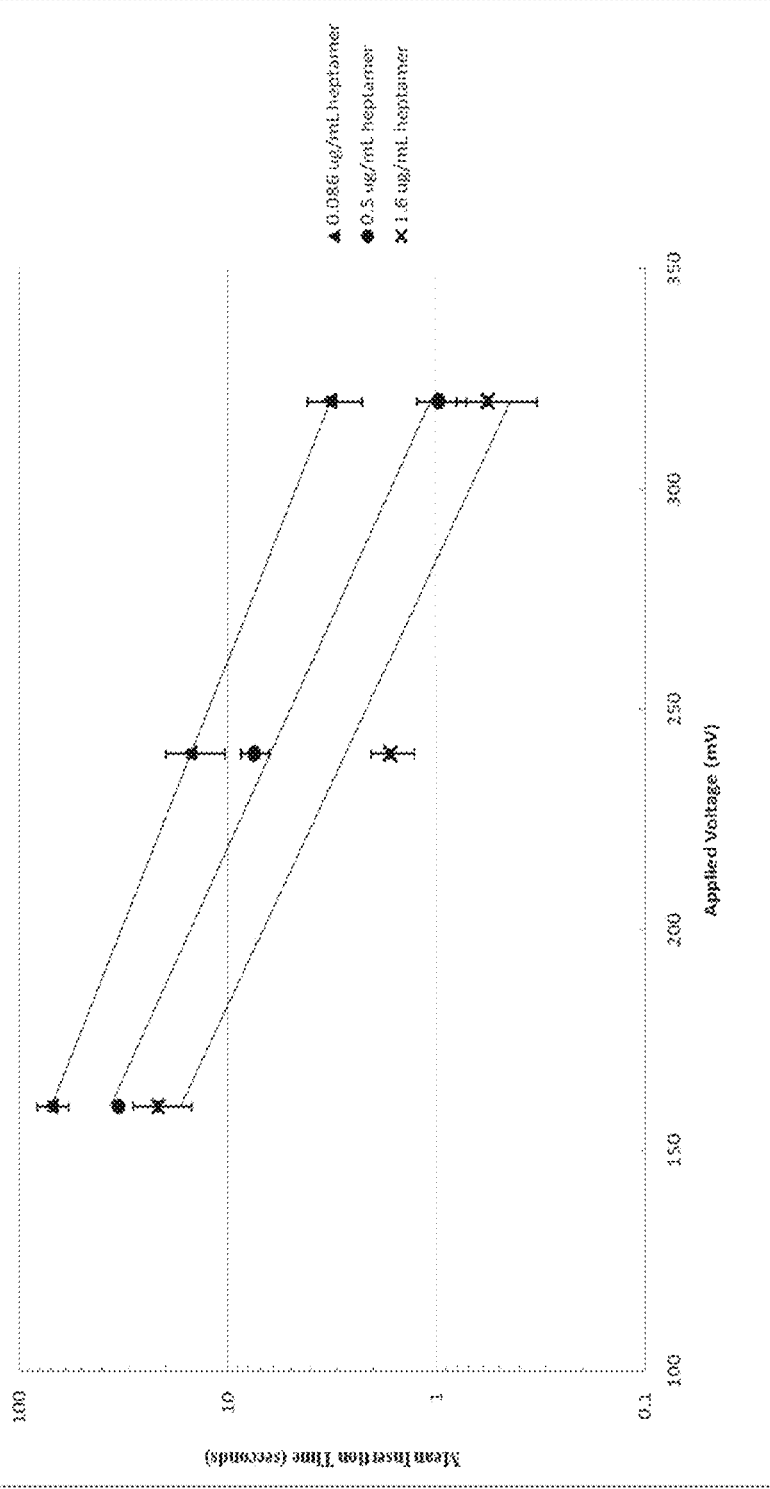
FIG. 8 illustrates the voltage dependence of the mean time to insertion of M113K, K8A alpha-HL into a PLB using three different alpha-HL concentrations. Experimental details and results are described in Example 4.

The results of additional experiments demonstrating the mean time to insertion as a function of applied voltage with three varying alpha-HL concentrations (~240 pM, ~1.4 nM, and ~4.5 nM) are shown in FIG. 8. The plot shows a similar insertion time decrease as the voltage is increased from 160 mV to 320 mV. The plot also shows that an ~18 fold decrease in concentration (4.5 nM (1.6 ug/mL) to 240 pM (0.086 ug/mL) produces an ~3 fold increase in insertion time at 160 mV. The increase in bias voltage to 320 mV yields a decrease in insertion time to about 3 seconds, which is a significant improvement over the insertion time at 160 mV (e.g., approximately 70 seconds). Thus, with decreased protein concentrations, voltage can be effectively used to decrease the insertion time to levels acceptable for ion channel measurements.

Example 5

Table of Amino Acid and Nucleotide Sequences

Provided in the table hereafter are non-limiting examples of certain nucleotide sequences and amino acid sequences.

| SEQ ID NO | Description | Sequence |
| --- | --- | --- |
| SEQ ID NO: 1 | Wild type Alpha Hemolysin (Alpha-HL) Amino acid | adsdiniktgttdigsnttvktgdlvtydkengmhkkvfysfiddknhnkkllvirtkgt iagqyrvyseeganksglawpsafkvqlqlpdnevaqisdyyprnsidtkeymstltygf ngnvtgddtgkiggliganvsightlkyvqpdfktilesptdkkvgwkvifnnmvnqnwg pydrdswnpvygnqlfmktrngsmkaadnfldpnkassllssgfspdfatvitmdrkask qqtnidviyervrddyqlhwtstnwkgtntkdkwtdrsserykidwekeemtn |
| SEQ ID NO: 2 | Modified Alpha-HL (M113K) Amino acid | adsdiniktgttdigsnttvktgdlvtydkengmhkkvfysfiddknhnkkllvirtkgt iagqyrvyseeganksglawpsafkvqlqlpdnevaqisdyyprnsidtkeykstltygf ngnvtgddtgkiggliganvisightlkyvqpdfktilesptdkkvgwkvifnnmvnqnw gpydrdswnpvygnqlfmktrngsmkaadnfldpnkassllssgfspdfatvitmdrkas kqqtnidviyervrddyqlhwtstnwkgtntkdkwtdrsserykidwekeemtn |
| SEQ ID NO: 3 | Wild type Alpha Hemolysin (Alpha-HL) Nucleotide | ATGGCAGATTCTGATATTAATATTAAAACCGGTACTACAGATATTGGAAGCAATACTACA GTAAAAACAGGTGATTTAGTCACTTATGATAAAGAAAATGGCATGCACAAAAAAGTATTT TATAGTTTTATCGATGATAAAAATCACAATAAAAAACTGCTAGTTATTAGAACGAAAGGT ACCATTGCTGGTCAATATAGAGTTTATAGCGAAGAAGGTGCTAACAAAAGTGGTTTAGCC TGGCCTTCAGCCTTTAAGGTACAGTTGCAACTACCTGATAATGAAGTAGCTCAAATATCT GATTACTATCCAAGAAATTCGATTGATACAAAAGAGTATATGAGTACTTTAACTTATGGA TTCAACGGTAATGTTACTGGTGATGACAGGAAAAATTGGCGGCCTTATTGGTGCAAAT GTTTCGATTGGTCATACACTGAAATATGTTCAACCTGATTTCAAAACAATTTTAGAGAGC CCAACTGATAAAAAAGTAGGCTGGAAAGTGATATTTAACAATATGGTCAATCAAATTGG GGACCATATGATAGAGATTCTTGGAACCCGGTATATGGCAATCAACTTTTCATGAAAACT GAAAATGGTTCTATGAAAGCAGCAGATAACTTCCTTGATCCTAACAAAGCAAGTTCTCTA TTATCTTCAGGGTTTTCACCAGACTTCGCTACAGTTATTACTATGGATAGAAAAGCATCC AAACAACAAACAAATATAGATGTAATATACGAACGAGTTCGTGATGATTACCAATTGCAT TGGACTTCAACAAATTGGAAAGGTACCAATACTAAAGATAAATGGACAGATCGTTCTTCA GAAAGATATAAAATCGATTGGGAAAAAGAAGAAATGACAAATTAA |
| SEQ ID NO: 4 | Modified Alpha-HL (M113K) Nucleotide | ATGGCAGATTCTGATATTAATATTAAAACCGGTACTACAGATATTGGAAGCAATACTACA GTAAAAACAGGTGATTTAGTCACTTATGATAAAGAAAATGGCATGCACAAAAAAGTATTT TATAGTTTTATCGATGATAAAAATCACAATAAAAAACTGCTAGTTATTAGAACGAAAGGT ACCATTGCTGGTCAATATAGAGTTTATAGCGAAGAAGGTGCTAACAAAAGTGGTTTAGCC TGGCCTTCAGCCTTTAAGGTACAGTTGCAACTACCTGATAATGAAGTAGCTCAAATATCT GATTACTATCCAAGAAATTCGATTGATACAAAAGAGTATAAGAGTACTTTAACTTATGGA TTCAACGGTAATGTTACTGGTGATGACAGGAAAAATTGGCGGCCTTATTGGTGCAAAT GTTTCGATTGGTCATACACTGAAATATGTTCAACCTGATTTCAAAACAATTTTAGAGAGC CCAACTGATAAAAAAGTAGGCTGGAAAGTGATATTTAACAATATGGTCAATCAAATTGG GGACCATATGATAGAGATTCTTGGAACCCGGTATATGGCAATCAACTTTTCATGAAAACT GAAAATGGTTCTATGAAAGCAGCAGATAACTTCCTTGATCCTAACAAAGCAAGTTCTCTA TTATCTTCAGGGTTTTCACCAGACTTCGCTACAGTTATTACTATGGATAGAAAAGCATCC AAACAACAAACAAATATAGATGTAATATACGAACGAGTTCGTGATGATTACCAATTGCAT TGGACTTCAACAAATTGGAAAGGTACCAATACTAAAGATAAATGGACAGATCGTTCTTCA GAAAGATATAAAATCGATTGGGAAAAAGAAGAAATGACAAATTAA |

Example 6

Examples of Embodiments

Provided hereafter are non-limiting examples of certain embodiments of the technology.

A1. A method, comprising:
contacting a PLB with a protein capable of inserting into the lipid bilayer;
applying an insertion voltage of about 160 mV or greater;
monitoring for the insertion of a protein into the PLB; and
reducing the voltage to less than the insertion voltage after an insertion is observed.

A2. The method of embodiment A1, wherein reducing the voltage comprises reducing the voltage by at least 1 mV less than the insertion voltage.

B1. A method, comprising:
contacting a PLB disposed between electrodes with a protein capable of inserting into the lipid bilayer;
applying an insertion voltage between the electrodes of about 160 mV or greater;
monitoring for the insertion of a protein into the PLB; and
reducing the voltage to less than the insertion voltage once an insertion is observed.

B2. The method of embodiment B2, wherein the voltage is reduced to at least 1 mV less than the insertion voltage.

C1. The method of any one of embodiments A1 to B2 which comprises toggling the voltage.

C2. The method of embodiment C1, wherein the voltage is toggled until protein insertion into the bilayer is identified.

C3. The method of embodiment C1 or C2, wherein a positive voltage bias is included in the toggling.

C4. The method of embodiment C1 or C2, wherein a negative voltage bias is included in the toggling.

C5. The method of embodiment C1 or C2, wherein a positive voltage bias and a negative voltage bias is included in the toggling.

C6. The method of embodiment C5, wherein the positive voltage bias and the negative voltage bias are alternated.

C7. The method of any one of embodiments C1 to C6, wherein each cycle in the toggling includes applying an insertion voltage bias followed by applying a measurement voltage bias.

C8. The method of any one of embodiments C1 to C7, wherein the voltage is toggled multiple times.

C9. The method of embodiment C8, wherein the voltage is toggled about 2 times to about 1,000,000 times.

C10. The method of embodiment C8 or C9, wherein each toggle cycle is about 1 millisecond to about 5 seconds.

C11. The method of any one of embodiments C8, C9 and C10, wherein the voltage is toggled in a timeframe of about 1 milliseconds to about 180 minutes.

D1. The method of any one of embodiments A1, B1 and C1 to C10, wherein the protein comprises a pore or channel.

D2. The method of embodiment D1, wherein the protein is an ion channel protein.

D3. The method of embodiment D1, wherein the protein is a porin protein.

D4. The method of embodiment D3, wherein the a nucleic acid is translocated through the porin protein.

D5. The method of embodiment D3, wherein the porin protein is a hemolysin protein.

D6. The method of embodiment D5, wherein the porin protein is a bacterial hemolysin protein.

D7. The method of embodiment D6, wherein the porin protein is an alpha hemolysin protein.

D8. The method of any one of embodiments D1 to D7, wherein the protein is a native protein.

D9. The method of any one of embodiments D1 to D7, wherein the protein includes one or more amino acid insertions, deletions or substitutions with respect to a native counterpart.

E1. The method of any one of embodiments A1, B1, C1 to C10 and D1 to D9, which comprises monitoring for insertion of the protein into the lipid bilayer.

E2. The method of embodiment E1, wherein the insertion is identified by a stable current at an open pore current.

E3. The method of embodiment E2, wherein the protein is in contact with a ligand and the ligand translocates the protein.

E4. The method of embodiment E3, wherein the ligand comprises a nucleic acid.

E5. The method of embodiment E1, wherein the insertion is identified by a protein blocking event.

E6. The method of embodiment E1, wherein the insertion is identified by one or more transient voltage spikes.

F1. The method of any one of embodiments A1, B1, C1 to C10, D1 to D9 and E1 to E6, wherein the voltage of about 160 mV or greater is about 200 mV to about 2000 mV.

F2. The method of any one of embodiments A1, B1, C1 to C10, D1 to D9 and E1 to E6, wherein the voltage of about 160 mV or greater is about 320 mV to about 2000 mV.

F3. The method of embodiment F1, wherein the voltage of about 160 mV or greater is about 350 mV.

F4. The method of any one of embodiments A1, B1, C1 to C10, D1 to D9, E1 to E6, F1 to F3, wherein the PLB spans a channel or nanopore, or an aperture of a channel or nanopore, in a nanopore membrane system.

F5. The method of embodiment F4, wherein the PLB spans at least two channels or nanopores in the nanopore membrane system.

F6. The method of embodiment F4 or F5, wherein the aperture of the channel or nanopore has a diameter of about 0.25 nanometers to about 50 micrometers.

F7. The method of embodiment F4 or F5, wherein the aperture of the channel or nanopore has a diameter of about 0.25 nanometers to about 10 micrometers.

F8. The method of any one of embodiments A1, B1, C1 to C10, D1 to D9, E1 to E6, and F1 to F7, wherein a single protein inserts into the PLB.

F9. The method of any one of embodiments A1, B1, C1 to C10, D1 to D9, E1 to E6, and F1 to F8, wherein reducing the voltage to less than the insertion voltage once an insertion is observed prevents additional protein insertions from occurring.

F10. The method of any one of embodiments A1, B1, C1 to C10, D1 to D9, E1 to E6, and F1 to F9, wherein the protein is incorporated into a vesicle prior to contacting the protein with the PLB.

F11. The method of any one of embodiments A1, B1, C1 to C10, D1 to D9, E1 to E6, and F1 to F10, which is conducted at a substantially constant backpressure.

F12. The method of any one of embodiments A1, B1, C1 to C10, D1 to D9, E1 to E6, and F1 to F11, wherein the protein concentration is about 0.001 femtomolar to about 10 millimolar.

F13. The method of any one of embodiments A1, B1, C1 to C10, D1 to D9, E1 to E6, and F1 to F12, wherein the PLB contacted with the protein prior to applying an electrical bias includes substantially no inserted protein.

F14. The method of any one of embodiments A1, B1, C1 to C10, D1 to D9, E1 to E6, and F1 to F13, wherein the protein is stably inserted into the PLB for a period of time.

F15. The method of embodiment F14, wherein the period of time is about 1 minute or greater.

F16. The method of embodiment F14, wherein the period of time is about 1 hour or greater.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claims that follow.

What is claimed is:

1. A method for inserting a protein into a planar lipid bilayer, comprising:
   contacting a planar lipid bilayer (PLB) with a protein capable of inserting into the lipid bilayer;
   applying an insertion voltage of about 320 mV to about 2000 mV;
   monitoring for the insertion of the protein into the PLB; and
   reducing the voltage to less than the insertion voltage after the insertion is observed.

2. The method of claim 1, wherein reducing the voltage comprises reducing the voltage by at least 1 mV less than the insertion voltage.

3. The method of claim 1, which comprises toggling the voltage.

4. The method of claim 3, wherein the voltage is toggled until protein insertion into the bilayer is identified.

5. The method of claim 3, wherein toggling comprises a positive voltage bias.

6. The method of claim 3, wherein the toggling comprises a negative voltage bias.

7. The method of claim 3, wherein the toggling comprises a positive voltage bias and a negative voltage bias.

8. The method of claim 7, wherein the positive voltage bias and the negative voltage bias are alternated.

9. The method of claim 3, wherein the toggling comprises one or more cycles and each cycle comprises applying an insertion voltage bias followed by applying a measurement voltage bias.

10. The method of claim 3, wherein the voltage is toggled about 2 times to about 1,000,000 times.

11. The method of claim 1, wherein the protein is an alpha hemolysin protein.

12. The method of claim 1, wherein the insertion is identified by a stable current at an open pore current.

13. The method of claim 1, wherein the insertion is identified by a protein blocking event.

14. The method of claim 1, wherein the voltage is about 350 mV.

15. The method of claim 1, wherein the PLB spans an aperture of a channel in a nanopore membrane system.

16. The method of claim 15, wherein the channel has a diameter of about 1.0 nanometers to about 10 micrometers.

17. The method of claim 1, wherein a single protein inserts into the PLB.

18. The method of claim 1, wherein reducing the voltage to less than the insertion voltage once an insertion is observed prevents additional protein insertions from occurring.

* * * * *